(12) United States Patent
Schneck et al.

(10) Patent No.: US 7,973,137 B1
(45) Date of Patent: Jul. 5, 2011

(54) CELL COMPOSITIONS COMPRISING MOLECULAR COMPLEXES THAT MODIFY IMMUNE RESPONSES

(75) Inventors: Jonathan Schneck, Silver Spring, MD (US); Sean O'Herrin, Baltimore, MD (US); Michael S. Lebowitz, Pikesville, MD (US); Abdel Hamad, Ellicott City, MD (US)

(73) Assignee: Johns Hopkins University, Baltimore, MD (US)

( * ) Notice: Subject to any disclaimer, the term of this patent is extended or adjusted under 35 U.S.C. 154(b) by 1423 days.

(21) Appl. No.: 09/642,660

(22) Filed: Aug. 22, 2000

Related U.S. Application Data

(63) Continuation of application No. 09/074,276, filed on May 7, 1998, now Pat. No. 6,082,792, which is a continuation-in-part of application No. 08/828,712, filed on Mar. 28, 1997, now Pat. No. 6,015,884.

(60) Provisional application No. 60/014,367, filed on Mar. 28, 1996.

(51) Int. Cl.
C12P 21/08 (2006.01)
(52) U.S. Cl. .................................................. 530/387.3
(58) Field of Classification Search ............... 435/320.1, 435/325; 424/93.1, 178.1; 530/387.3, 383.1
See application file for complete search history.

(56) References Cited

U.S. PATENT DOCUMENTS

| | | | |
|---|---|---|---|
| 5,583,031 A | 12/1996 | Stern | |
| 6,015,884 A | 1/2000 | Schneck et al. | |
| 6,140,113 A | 10/2000 | Schneck et al. | |
| 6,268,411 B1 | 7/2001 | Schneck et al. | |
| 6,269,411 B1 | 7/2001 | Reasoner | |
| 6,448,071 B1 | 9/2002 | Schneck et al. | |
| 6,458,354 B1 | 10/2002 | Schneck et al. | |
| 6,787,154 B2 | 9/2004 | Albani | |
| 2002/0006903 A1 | 1/2002 | Schneck et al. | |
| 2002/0119121 A1 | 8/2002 | Vitiello et al. | |
| 2002/0122818 A1 | 9/2002 | Albani | |
| 2003/0077248 A1 | 4/2003 | Moriarty et al. | |

FOREIGN PATENT DOCUMENTS

| | | | |
|---|---|---|---|
| WO | 93/10220 | | 5/1993 |
| WO | WO 93/10220 | * | 5/1993 |
| WO | WO 94/09131 | * | 4/1994 |
| WO | 96/04314 | | 2/1996 |
| WO | WO 00/40968 | | 7/2000 |
| WO | WO 01/80833 | | 11/2001 |
| WO | WO 01/94944 | | 12/2001 |
| WO | WO 02/065992 | | 8/2002 |
| WO | WO 03/057171 | | 7/2003 |

OTHER PUBLICATIONS

Burgess et al (J of Cell Bio. 111:2129-2138, 1990).*
Zwirner J et al (J. Immunol. Jan. 1992;148(1):272-276).*
Kuwana et al (Biochem Biophys Res Commun Dec. 1987;149(3):960-968).*
Seimiya H et al (J Biochem (Tokyo) Jun. 1993;113(6):687-91).*
Matsui et al (Proc. Natl. Acad. Sci., USA, 91(26)12862-12866, Dec. 20, 1994).*
J. Dal Porto et al. "A soluble divalent class I major histocompatibility complex molecule inhibits alloreactive T cells at nanomolar concentrations" Proceedings of the National Academy of Science of the USA vol. 90, No. 14, Jul. 15, 1993 pp. 6671-6675.
T. Johansen et al. "Potent inhibition of alloreactive T cells by nanomolar concentrations of a divalent soluble class I MHC molecule" The Journal of Immunology, vol. 150, No. 8, part 2, Apr. 15, 1993, p. 83A.
C. Gregoire et al. "Engineered secreted T-cell receptor alpha-beta heterodimers" Proceedings of the National Academy of Sciences of the USA vol. 88, No. 18, Sep. 15, 1991, pp. 8077-8081.
D. Eilat et al. "Secretion of a soluble, chimeric gamma-delta T-cell receptor-immunoglobulin heterodimer" Proceedings of the National Academy of Sciences of the USA, vol. 89, No. 15, Aug. 1, 1992, pp. 6871-6875.
S. Weber et al. "Specific low-affinity recognition of major histocompatibility complex plus peptide by soluble T-cell receptor" Nature, vol. 356, No. 6372, Apr. 30, 1992, pp. 792-976.
H-C Chang et al. "A general method for facilitating heterodimeric pairing between two proteins: Application to expression of alpha and beta T-cell receptor extracellular segments" Proceedings of the National Academy of Sciences of the USA, vol. 91, Nov. 1994, pp. 11408-11412.
S. O'Herrin et al. "Expression and analysis of soluble MHC- and TcR-immunoglobulin super dimers" The FASEB Journal, vol. 10, No. 6, Apr. 30, 1996 p. A1473.
J. Schneck et al. "Specific inhibition of graft rejection by soluble MHC superdimers" The FASEB Journal, vol. 10, No. 6, Apr. 30, 1996, p. A1473.
M. Lebowitz et al. "Specificity of soluble 2C TcR/Ig superdimers for peptide/MHC complexes" The FASEB Journal, vol. 10, No. 6, Apr. 30, 1996, p. A1178.
U.S. Appl. No. 09/642,660, Schneck et al. Goldberg et al., "In vivo Augmentation of Tumor-Specific CTL Responses by Class I/Peptide Antigen Complexes on Microspheres (Large Multivalent Immunogen)," J. Immunol. 170, 228-35, 2003.
Latouche & Sadelain, "Induction of human cytotoxic T lymphocytes by artifical antigen-presenting cells," Nature Biotechnol. 18, 405-09, Apr. 2000.
Levine et al., "Effects of CD28 Costimulation on Long-Term Proliferation of CD4+ T cells in the Absence of Exogenous Feeder Cells," J. Immunol. 159, 5921-30, 1997.
Maus et al., "Ex vivo expansion of polyclonal and antigen-specific cytotoxic T lymphocytes by artificial APCs expressing ligands for the T-cell receptor, CD28 and 4-1BB," Nature Biotechnol. 20, 143-48, Feb. 2002.

(Continued)

Primary Examiner — Sean E Aeder
(74) Attorney, Agent, or Firm — Banner & Witcoff, Ltd.

(57) ABSTRACT

Compositions comprising a cell in which a molecular complex with high affinity for its cognate ligand is bound to the surface of the cell are provided. To form the molecular complexes, extracellular domains of transmembrane heterodimeric proteins, particularly T cell receptor and major histocompatibility complex proteins, can be covalently linked to the heavy and light chains of immunoglobulin molecules. The molecular complexes can be used, inter alia, to detect and regulate antigen-specific T cells and as therapeutic agents for treating disorders involving immune system regulation, such as allergies, autoimmune diseases, tumors, infections, and transplant rejection. Optionally, identical antigenic peptides can be bound to each ligand binding site of a molecular complex.

15 Claims, 21 Drawing Sheets

OTHER PUBLICATIONS

Maus et al., "HLA tetramer-based artificial antigen-presenting cells for stimulation of CD4+ T cells," *Clin. Immunol. 106*, 16-22, 2003.

Nakamura et al., "Dendritic cells genetically engineered to simultaneously express endogenous tumor antigen and granulocyte macrophage colony-stimulating factor elicit potent therapeutic anti-tumor immunity", *Clinical Cancer Research: An Official Journal of the American Association for Cancer Research*, vol. 8, No. 8, Aug. 2002, pp. 2742-2749.

Oelke et al., "Ex vivo induction and expansion of antigen-specific cytotoxic T cells by HLA-Ig-coated artificial antigen-presenting cells", *Nature Medicine*, vol. 9, No. 5, May 2003, pp. 619-624.

Oelke et al., "Generation and purification of CD8+ melan-A-specific cytotoxic T lymphocytes for adoptive transfer in tumor immunotherapy", *Clinical Cancer Research; An Official Journal of the American Association for Cancer Research*, May 2000, vol. 6, No. 5, pp. 1997-2005.

Von Bergwelt-Baildon et al., "Human primary and memory cytotoxic T lymphocyte responses are effectively induced by means of CD40-activated B cells as antigen-presenting cells: Potential for clinical application", *Blood*, vol. 99, No. 9, May 1, 2002, pp. 3319-3325.

Deeths et al., "B7-1-Dependent co-stimulation results in qualitatively and quantitatively different responses by CD4+ and CD8+ T cells", European Journal of Immunology, vol. 27, No. 3, 1997, pp. 598-608.

Oertli et al., "Artificial antigen-presenting cells engineered by recombinant vaccinia viruses expressing antigen, MHC class II, and costimulatory molecules elicit proliferation of CD4+lymphocytes invitro", Clinical and Experimental Immunology, vol. 110, No. 1, Oct. 1997, pp. 144-149.

\* cited by examiner

US 7,973,137 B1

CELL COMPOSITIONS COMPRISING MOLECULAR COMPLEXES THAT MODIFY IMMUNE RESPONSES

This application is a continuation of U.S. Ser. No. 09/074,276, filed May 7, 1998 now U.S. Pat. No. 6,082,792 which is a continuation-in-part of U.S. Ser. No. 08/828,712, filed Mar. 28, 1997, now U.S. Pat. No. 6,015,884 and claims the benefit of U.S. Ser. No. 60/014,367, filed Mar. 28, 1996.

BACKGROUND OF THE INVENTION

Generation of soluble divalent or multivalent molecular complexes comprising MHC class II or T cell receptors (TCR) is complicated by the fact that such complexes are formed by heterodimeric integral membrane proteins. Each of these protein complexes consists of α and β integral membrane polypeptides which bind to each other, forming a functional unit involved in immune recognition. While both class II MHC and TCR molecules have stable, disulfide-containing immunoglobulin domains, obtaining them in properly folded form in the absence of their respective integral membrane regions has proven to be difficult (6, 12).

Strategies have been developed to facilitate subunit pairing and expression of soluble analogs of integral membrane heterodimeric complexes (for review, see 4). Initially, the extracellular domains of a TCR (5, 6) or class II MHC (7) were linked via glycosylphosphatidylinositol (GPI) membrane anchor sequences, resulting in surface expression of the polypeptide chains to enhance subunit pairing. Subsequent enzymatic cleavage resulted in the release of soluble monovalent heterodimers from the GPI anchors. Another strategy facilitated pairing by covalent linkage of immunoglobulin light chain constant regions to constant regions of the TCR α and β chains (8). Direct pairing of the α and β chains of a TCR during synthesis has also been accomplished by covalent linkage of the variable regions of the α and β chains spaced by a 25 amino acid spacer (9) or by linking the variable region of the a chain to the extracellular VβCβ chain with a 21 amino acid spacer (10). This strategy, too, results in monomers. In several constructs, α/β dimerization was facilitated by covalent linkage of the leucine zipper dimerization motif to the extracellular domains of the α and β polypeptides of TCR or class II MHC (11-13). Pairing of the extracellular domains of the α and β chains of class II MHC has also been achieved after the chains were produced in separate expression systems (14, 15). However, the utility of these probes is limited by their intrinsic low affinity for cognate ligands.

Approaches have also been developed to generate probes for antigen-specific T cells. The first approach used to develop specific reagents to detect clonotypic TCRs was the generation of high affinity anticlonotypic monoclonal antibodies. Anticlonotypic monoclonal antibodies discriminate on the basis of specific TCR Vα and Vβ conformational determinants, which are not directly related to antigenic specificity. Therefore, an anticlonotypic antibody will interact with only one of potentially many antigen-specific different clonotypic T cells that develop during an immune response.

The development of reagents which differentiate between specific peptide/MHC complexes has also been an area of extensive research. Recently, investigators have used soluble monovalent TCR to stain cells by crosslinking TCRs with avidin after they have been bound to a cell (10). Another approach has been to generate monoclonal antibodies which differentiate between MHC molecules on the basis of peptides resident in the groove of the MHC peptide binding site. While theoretically this approach is appealing, such antibodies have been difficult to generate. Conventional approaches have produced only a few such antibodies with anti-peptide/MHC specificity (36-38). It is not clear why this is the case, but the difficulty may reflect the fact that peptides are generally buried within the MHC molecule.

Two new approaches have been developed to obtain peptide-specific, MHC dependent monoclonal antibodies. One approach utilizes a recombinant antibody phage display library to generate antibodies which have both peptide-specificity and MHC restriction (42). In the second approach, mice are immunized with defined peptide/MHC complexes, followed by screening of very large numbers of the resultant monoclonal antibodies (43, 44). However, the need to screen large numbers of monoclonal antibodies is a disadvantage of this method.

Thus, there is a need in the art for soluble, multivalent molecular complexes with high affinity for antigenic peptides which can be used, for example, to detect and regulate antigen-specific T cells and as therapeutic agents for treating disorders involving immune system regulation.

SUMMARY OF THE INVENTION

It is an object of the present invention to provide reagents which specifically and stably bind to and modulate antigen-specific T cells. These and other objects of the invention are provided by one or more of the embodiments described below.

One embodiment of the invention provides a molecular complex which comprises at least four fusion proteins. Two first fusion proteins comprise an immunoglobulin heavy chain and an extracellular domain of a first transmembrane polypeptide. The immunoglobulin heavy chain comprises a variable region. Two second fusion proteins comprise an immunoglobulin light chain and an extracellular domain of a second transmembrane polypeptide. The fusion proteins associate to form the molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein.

Another embodiment of the invention provides a polynucleotide. The polynucleotide encodes a first and a second fusion protein. The first fusion protein comprises an immunoglobulin heavy chain and an extracellular domain of a first transmembrane polypeptide of a heterodimeric protein. The immunoglobulin heavy chain comprises a variable region. The immunoglobulin light chain is C-terminal to the extracellular domain of the first transmembrane polypeptide. The second fusion protein comprises an immunoglobulin light chain and an extracellular domain of a second transmembrane polypeptide of the heterodimeric protein. The immunoglobulin light chain is C-terminal to the extracellular portion of the second transmembrane polypeptide. The extracellular domains of the first and second transmembrane polypeptides form a ligand binding site.

Still another embodiment of the invention provides a host cell comprising at least one expression construct encoding a first and a second fusion protein. The first fusion protein comprises an immunoglobulin heavy chain and an extracellular domain of a first transmembrane polypeptide of a heterodimeric protein. The immunoglobulin heavy chain comprises a variable region wherein the immunoglobulin light chain is C-terminal to the extracellular domain of the first transmembrane polypeptide. The second fusion protein comprises an immunoglobulin light chain and an extracellular domain of a second transmembrane polypeptide of the heterodimeric protein. The immunoglobulin light chain is C-terminal to the extracellular portion of the second transmembrane polypeptide. The extracellular domains of the first and second transmembrane polypeptides form a ligand binding site. The affinity of the molecular complex for a cognate ligand is increased at least two-fold over a dimeric molecular complex consisting of a first and a second fusion protein.

Yet another embodiment of the invention provides a composition. The composition comprises a cell in which a molecular complex is bound to the surface of the cell. The molecular complex comprises at least four fusion proteins. Two first fusion proteins comprise an immunoglobulin heavy chain and an extracellular portion of a first transmembrane polypeptide. The immunoglobulin heavy chain comprises a variable region. Two second fusion proteins comprise an immunoglobulin light chain and an extracellular portion of a second transmembrane polypeptide. The fusion proteins associate to form a molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein.

A further embodiment of the invention provides a method for treating a patient suffering from an allergy. A molecular complex is administered to the patient at a dose sufficient to suppress or reduce a T cell response associated with the allergy. The molecular complex comprises at least four fusion proteins. Two first fusion proteins comprise an immunoglobulin heavy chain and an extracellular domain of a first transmembrane polypeptide. The immunoglobulin heavy chain comprises a variable region. Two second fusion proteins comprise an immunoglobulin light chain and an extracellular domain of a second transmembrane polypeptide. The fusion proteins associate to form a molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein. Each ligand binding site is bound to an antigenic peptide. The antigenic peptide is an antigen to which the patient has an allergic response.

Even another embodiment of the invention provides a method for treating a patient who has received or will receive an organ transplant. A molecular complex is administered to the patient at a dose sufficient to suppress or reduce an immune response to the organ transplant. The molecular complex comprises at least four fusion proteins. Two first fusion proteins comprise an immunoglobulin heavy chain and an extracellular domain of a first transmembrane polypeptide. The immunoglobulin heavy chain comprises a variable region. Two second fusion proteins comprise an immunoglobulin light chain and an extracellular domain of a second transmembrane polypeptide. The fusion proteins associate to form a molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein. Each ligand binding site is bound to an antigenic peptide. The antigenic peptide is an alloantigen.

Yet another embodiment of the invention provides a method for treating a patient suffering from an autoimmune disease. A molecular complex is administered to the patient at a dose sufficient to suppress or reduce the autoimmune response. The molecular complex comprises at least four fusion proteins. Two first fusion proteins comprise an immunoglobulin heavy chain and an extracellular domain of a first transmembrane polypeptide. The immunoglobulin heavy chain comprises a variable region. Two second fusion proteins comprise an immunoglobulin light chain and an extracellular domain of a second transmembrane polypeptide. The fusion proteins associate to form a molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein. Each ligand binding site is bound to an antigenic peptide. The antigenic peptide is one to which the patient expresses an autoimmune response.

Another embodiment of the invention provides a method for treating a patient having a tumor. A molecular complex is administered to the patient at a dose sufficient to induce or enhance an immune response to the tumor. The molecular complex comprises at least four fusion proteins. Two first fusion proteins comprise an immunoglobulin heavy chain and an extracellular domain of a first transmembrane polypeptide. The immunoglobulin heavy chain comprises a variable region. Two second fusion proteins comprise an immunoglobulin light chain and an extracellular domain of a second transmembrane polypeptide. The fusion proteins associate to form a molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein. Each ligand binding site is bound to an antigenic peptide. The antigenic peptide is expressed on the tumor.

Still another embodiment of the invention provides a method for treating a patient having an infection caused by an infectious agent. A molecular complex is administered to the patient at a dose sufficient to induce or enhance an immune response to the infection. The molecular complex comprises at least four fusion proteins. Two first fusion proteins comprise an immunoglobulin heavy chain and an extracellular domain of a first transmembrane polypeptide. The immunoglobulin heavy chain comprises a variable region. Two second fusion proteins comprise an immunoglobulin light chain and an extracellular domain of a second transmembrane polypeptide. The fusion proteins associate to form a molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein. Each ligand binding site is bound to an antigenic peptide. The antigenic peptide is a peptide of the infectious agent.

Another embodiment of the invention provides a method of labeling antigen-specific T cells. A sample which comprises antigen-specific T cells is contacted with a molecular complex. The molecular complex comprises at least four fusion proteins. Two first fusion proteins comprise an immunoglobulin heavy chain and an extracellular domain of a first transmembrane polypeptide. The immunoglobulin heavy chain comprises a variable region. Two second fusion proteins comprise an immunoglobulin light chain and an extracellular domain of a second transmembrane polypeptide. The fusion proteins associate to form the molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein. Each ligand binding site is bound to an identical antigenic peptide. The antigenic peptide specifically binds to the antigen-specific T cells. The cells are labeled with the molecular complex.

Yet another embodiment of the invention provides a method of activating antigen-specific T cells. A sample which comprises antigen-specific T cells is contacted with a molecular complex. The molecular complex comprises at least four fusion proteins. Two first fusion proteins comprise an immunoglobulin heavy chain and an extracellular domain of a first transmembrane polypeptide. The immunoglobulin heavy chain comprises a variable region. Two second fusion proteins comprise an immunoglobulin light chain and an extracellular domain of a second transmembrane polypeptide. The fusion proteins associate to form the molecular complex. The molecular complex comprises two ligand binding sites. Each ligand binding site is formed by the extracellular domains of the first and second transmembrane polypeptides. The affinity of the molecular complex for a cognate ligand is increased at least two-fold over a dimeric molecular complex consisting of a first and a second fusion protein. Each ligand binding site is bound to an identical antigenic peptide. The antigenic peptide specifically binds to and activates the antigen-specific T cells.

Even another embodiment of the invention provides a method of labeling a specific peptide/MHC complex. A sample comprising a peptide/MHC complex is contacted with a composition comprising a molecular complex. The molecular complex comprises at least four fusion proteins. Two first fusion proteins comprise an immunoglobulin heavy chain and an extracellular domain of a TCR α chain. Two second fusion proteins comprise an immunoglobulin light chain and an extracellular domain of a TCR β chain. The fusion proteins associate to form a molecular complex. The molecular complex comprises two ligand binding sites. Each ligand binding site is formed by the extracellular domains of the TCR α and β chains. The affinity of the molecular complex for a cognate ligand is increased at least two-fold over a dimeric molecular complex consisting of a first and a second fusion protein. The ligand binding site specifically binds to and labels the peptide/MHC complex.

Thus, the present invention provides a general approach for producing soluble multivalent versions of heterodimeric proteins, such as T cell receptors and class II MHC molecules. These multivalent molecules can be used, inter alia, as diagnostic and therapeutic agents for treating immune disorders and to study cell-cell interactions which are driven by multivalent ligand-receptor interactions.

BRIEF DESCRIPTION OF THE DRAWINGS

FIG. 9A shows peptide-dependent 2C TCR/Ig reactivity. FIG. 9B shows peptide-dependent 30.5.7 reactivity.

FIGS. 16C and 16D show comparison of staining using either 2C TCR/Ig (FIG. 16C) or the anti-L$^d$ mAb 30.5.7 (FIG. 16D). For comparison, data presented are shown as mean channel fluorescence derived from individual histograms.

DETAILED DESCRIPTION OF THE INVENTION

Figure 1A:
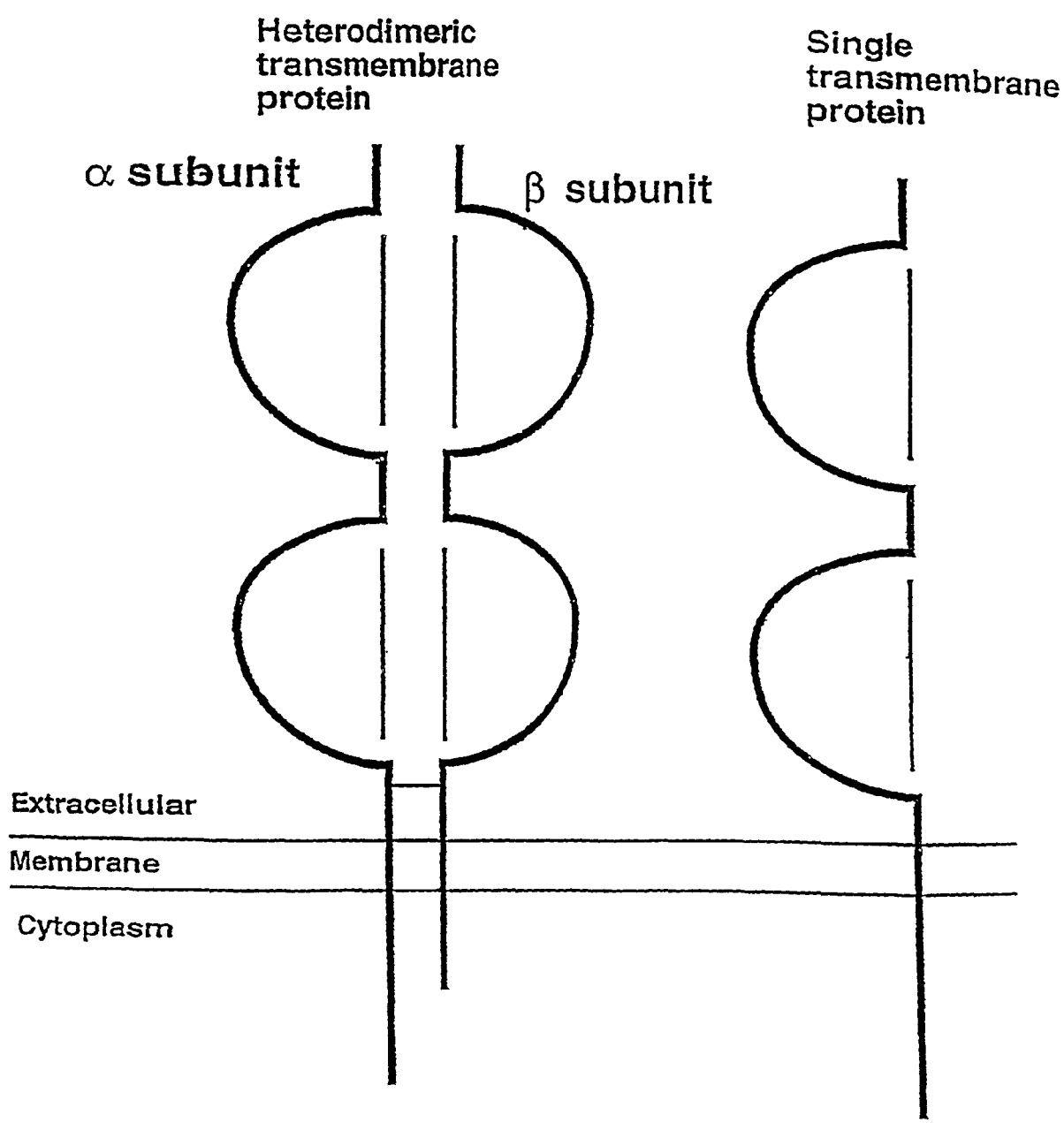
FIG. 1A. A typical configuration of a heterodimeric double transmembrane protein.

To enhance our ability to analyze and regulate antigen-specific immune responses, we have designed a general system for expression of soluble divalent or multivalent molecular complexes of heterodimeric proteins which form a ligand binding site, particularly MHC class II and TCR proteins. Successful expression of soluble molecular complexes with high avidity for their cognate ligands is achieved using an immunoglobulin as a molecular scaffolding structure. The immunoglobulin moiety serves as a scaffolding for proper folding of the α and β chains, without which nonfunctional aggregates would likely result, as previously described (4, 12). The physical proximity of the immunoglobulin heavy and light chains, whose folding and association is favored by a net gain in free energy, overcomes the entropy required to bring the soluble TCR or MHC α and β chains together to facilitate their folding. Furthermore, the intrinsic flexibility afforded by the immunoglobulin hinge region facilitates the binding of the ligand binding sites to their cognate ligands.

These structural features distinguish this design over methodologies which generate soluble monovalent complexes, in that they enable a multimeric interaction of, for example, at least two peptide/MHC complexes with at least two TCR molecules. This interaction has greater avidity than the interaction of TCR monomers with a peptide/MHC complex. Molecular complexes of the invention have the further advantage that, by altering the Fc portion of the immunoglobulin, different biological functions can be provided to the molecule based on biological functions afforded by the Fc portion.

In addition, soluble TCR/Ig molecular complexes of the invention can be used to define specific ligands recognized by T cells. These complexes have potential uses in defining ligands of γ/δ TCR or of undefined tumor-specific T cells. Furthermore, since T cell activation requires cross linking of multiple TCRs, interaction of TCR-Ig molecular complexes can mimic natural T cell activation, facilitating both induction and enhancement of immune responses and elucidation of biochemical interactions involved in TCR recognition of peptide/MHC complexes.

Molecular complexes of the invention have broader applications than regulation of immune system responses. For example, adhesion of cells mediated through the interactions of integrins can be modulated using soluble divalent molecular complexes comprising integrin molecules. Modulation of cytokine-mediated cell stimulation can also be achieved, employing soluble divalent molecular complexes comprising a cytokine receptor. Binding of the ligand binding site of the cytokine receptor to a soluble cytokine, for example, can inhibit the ability of the cytokine to mediate cellular proliferation.

Molecular complexes of the invention comprise an immunoglobulin scaffold and at least two ligand binding sites. The ligand binding sites are formed by the extracellular domains of two transmembrane polypeptides. The transmembrane polypeptides can be any transmembrane polypeptides which form a heterodimeric protein and which can bind a ligand, preferably an antigenic peptide. Suitable heterodimeric proteins which can provide transmembrane polypeptides for use in molecular complexes of the invention include MHC class II molecules, T cell receptors, including α/β and γ/δ T cell receptors, integrin molecules, and cytokine receptors, such as receptors for IL-2, IL-3, IL-4, IL-7, IL-9, erythropoietin, leukemia inhibitory factor, granulocyte colony stimulating factor, oncostatin M, ciliary neurotrophic factor, growth hormone, and prolactin.

Molecular complexes of the invention comprise at least four fusion proteins. Two fusion proteins comprise an immunoglobulin heavy chain, including a variable region, and an extracellular domain of a first transmembrane polypeptide, such as an MHC class IIβ chain or a TCR α chain. Two fusion proteins of the molecular complex comprise an immunoglobulin κ or λ light chain and an extracellular domain of a second transmembrane polypeptide, such as an MHC class IIα chain or a TCR β chain. The fusion proteins associate to form the molecular complex. The affinity of the molecular complex for a cognate ligand is increased at least two-fold over a dimeric molecular complex consisting of a first and a second fusion protein. Preferably, the affinity is increased at least 5-, 10-, 20-, 25-, 30-, 35-, 40-, 50-, 75-, or 100-fold.

The immunoglobulin heavy chain can be the heavy chain of an IgM, IgD, IgG3, IgG1, IgG2β, IgG2α, IgE, or IgA. Preferably, an IgG1 heavy chain is used to form divalent molecular complexes comprising two ligand binding sites. A variable region of the heavy chain is included: IgM or IgA heavy chains can be used to provide pentavalent or tetravalent molecular complexes, respectively. Molecular complexes with other valencies can also be constructed, using multiple immunoglobulin chains.

Fusion proteins which form molecular complexes of the invention can comprise a peptide linker inserted between a variable region of an immunoglobulin chain and an extracellular domain of a transmembrane polypeptide. The length of the linker sequence can vary, depending upon the flexibility required to regulate the degree of antigen binding and cross-linking. Constructs can also be designed such that the extracellular domains of transmembrane polypeptides are directly and covalently attached to the immunoglobulin molecules without an additional linker region. If a linker region is included, this region will preferably contain at least 3 and not more than 30 amino acids. More preferably, the linker is about 5 and not more than 20 amino acids; most preferably, the linker is less than 10 amino acids. Generally, the linker consists of short glycine/serine spacers, but any amino acid can be used. A preferred linker for connecting an immunoglobulin heavy chain to an extracellular portion of a first transmembrane protein is GLY-GLY-GLY-THR-SER-GLY (SEQ ID NO:10). A preferred linker for connecting an immunoglobulin light chain to an extracellular portion of a second transmembrane protein is GLY-SER-LEU-GLY-GLY-SER (SEQ ID NO:11).

Methods of making fusion proteins, either recombinantly or by covalently linking two protein segments, are well known. Preferably, fusion proteins are expressed recombinantly, as products of expression constructs. Expression constructs of the invention comprise a polynucleotide which encodes one or more fusion proteins in which an immunoglobulin chain is C-terminal to an extracellular domain of a transmembrane polypeptide. Polynucleotides in expression constructs of the invention can comprise nucleotide sequences coding for a signal sequence; expression of these constructs results in secretion of a fusion protein comprising the extracellular domain of the transmembrane polypeptide spliced to the intact variable region of the immunoglobulin molecule. Variations or truncations of this general structures in which one or more amino acids are inserted or deleted but which retain the ability to bind to the target ligand are encompassed in the present invention.

In a preferred embodiment, an expression construct comprises a baculovirus replication system, most preferably the baculovirus expression vector pAcUW51 (Pharmingen, California). This vector has two separate viral promoters, polyhedron and P10, allowing expression of both fusion proteins of a molecular complex in the same host cell. To facilitate cloning of different genes into the vector, multiple cloning sites can be introduced after each of the promoters. Optionally, expression constructs which each encode one fusion protein component of the molecular complex can be constructed.

Expression constructs of the invention can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

Host cells comprising expression constructs of the invention can be prokaryotic or eukaryotic. Bacterial systems for expressing fusion proteins of the invention include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad Sci. USA* (1983) 80: 21-25, and Siebenlist et al., *Cell* (1980) 20: 269.

Expression systems in yeast include those described in Ilinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 8: 142; Kunze et al., *J Basic Microbiol.* (1985) 25: 141; Gleeson et al., *J. Gen. Microbiol.* (1986) 132: 3459, Roggenkamp et al., *Mol. Gen. Genet.* (1986) 202:302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 8: 3376, U.S. Pat. No. 4,837,148, U.S. Pat. No. 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284-289; Tilburn et al., *Gene* (1983) 26: 205-221, Yelton et al., *Proc.*

*Natl. Acad. Sci. USA* (1984) 81: 1470-1474, Kelly and Hynes, *EMBO J.* (1985) 4: 475479; EP 244,234, and WO 91/00357.

Expression of fusion proteins of the invention in insects can be carried out as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765-776, Miller et al., *Ann. Rev. Microbiol.* (1988) 42: 177, Carbonell et al., *Gene* (1988) 73: 409, Maeda et al., *Nature* (1985) 315: 592-594, Lebacq-Verheyden et al., *Mol. Cell. Biol.* (1988) δ: 3129; Smith et al., *Proc. Natl. Acad. Sci. USA* (1985) 82: 8404, Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 8: 47-55, Miller et al., in GENETIC ENGINEERING (Setlow, J. K. et al. eds.), Vol. 8 (Plenum Publishing, 1986), pp. 277-279, and Maeda et al., *Nature*, (1985) 315: 592-594. A preferred method of expressing fusion proteins of the invention is described in Materials and Methods and in Example 1, below.

Expression of fusion proteins f the invention in mammalian cells can be achieved as described in Dijkema et al., *EMBO J.* (1985) 4: 761, Gorman et al., *Proc. Natl. Acad Sci. USA* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44, Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. RE 30,985.

Figure 3:
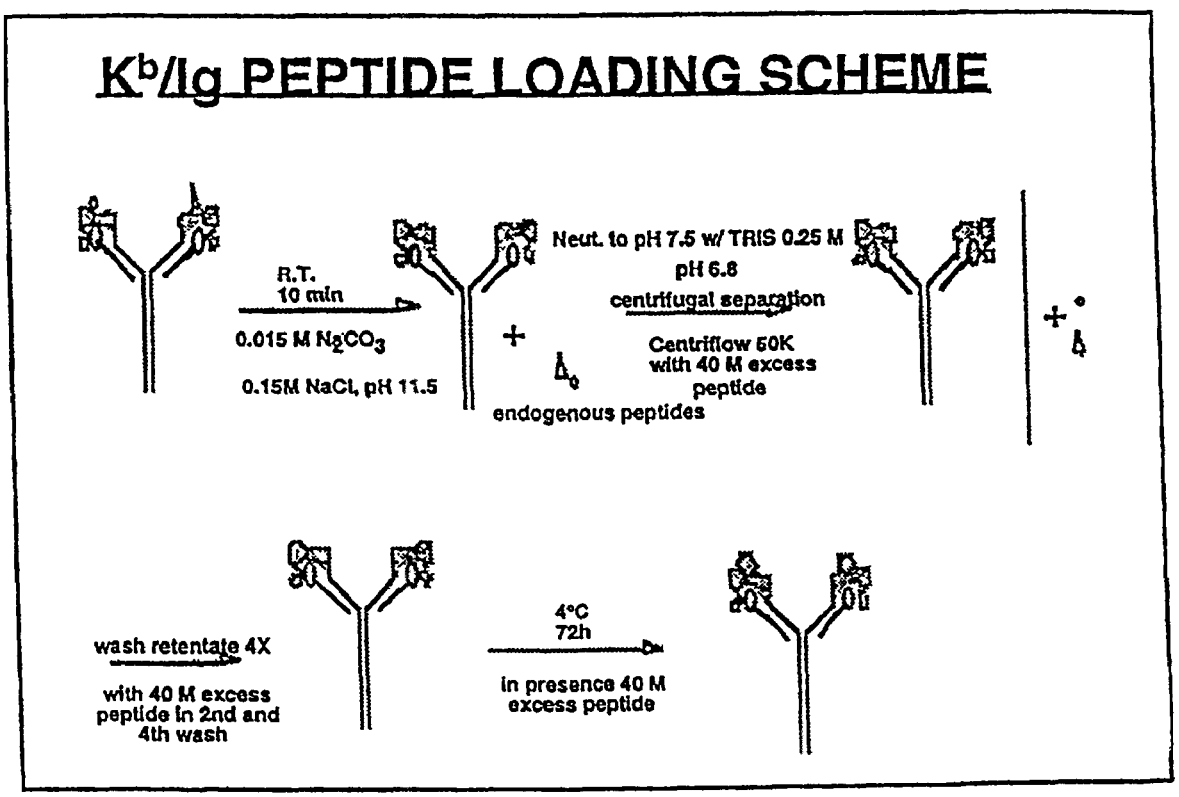
FIG. 3. Schematic of $K^b$/IgG loading scheme.
Figure 4:
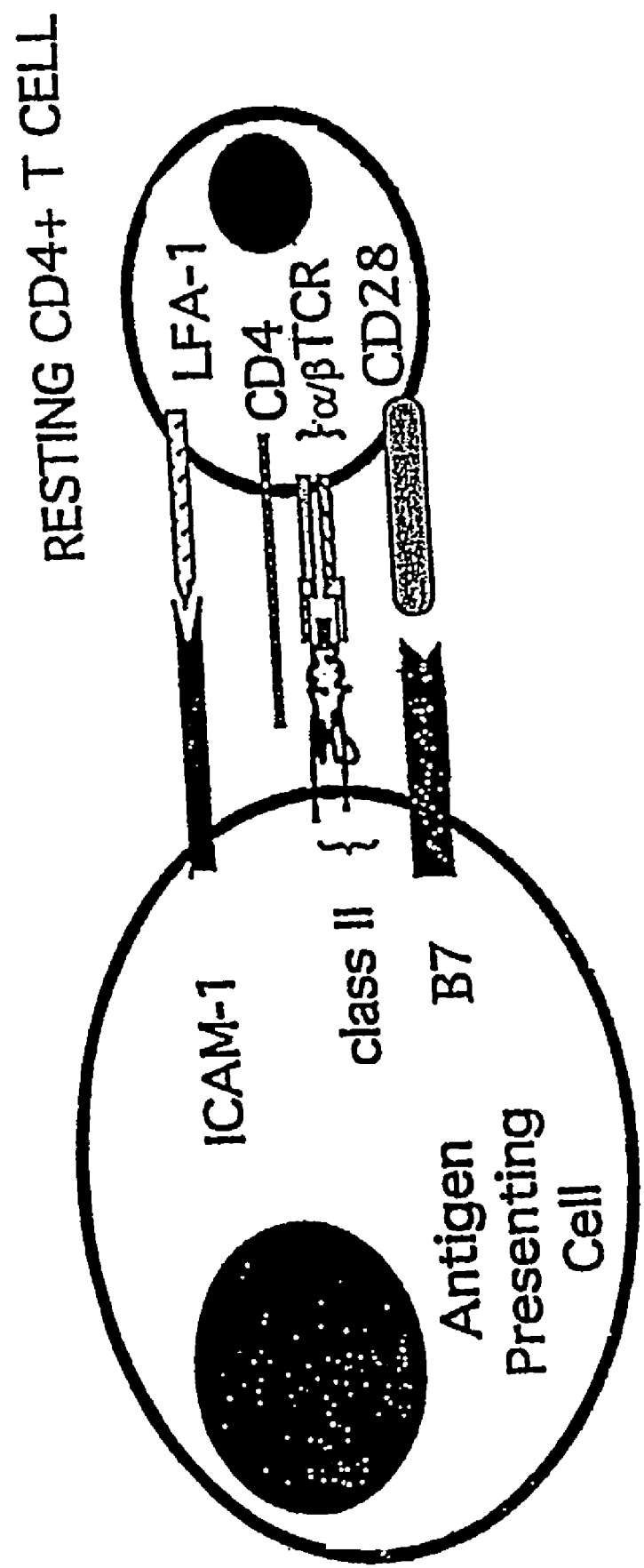
FIG. 4. Schematic of TCR/MHC interactions.

Ligand binding sites of molecular complexes can contain a bound ligand, preferably an antigenic peptide. Ligands can be passively bound to the ligand binding site, as described in Materials and Methods, below. Active binding can also be accomplished, for example, using alkaline stripping, rapid neutralization, and slow refolding of the molecular complex (see. FIG. 3 for a schematic). Ligands can also be covalently bound to the ligand binding site. Any peptide capable of inducing an immune response can be bound to the ligand binding site, including peptides which cause allergic or autoimmune responses, alloantigens, peptides which are expressed by tumors, and peptides of infectious agents, such as bacteria, viruses, or fungi. Identical antigenic peptides can be bound to each ligand binding site of a molecular complex.

Molecular complexes of the invention can be used diagnostically, to label antigen-specific cells in vitro or in vivo. A sample comprising antigen-specific T cells can be contacted with a molecular complex in which each ligand binding site is bound to an identical antigenic peptide. The sample can be, for example, peripheral blood, lymphatic fluid, lymph nodes, spleen, thymus, bone marrow, or cerebrospinal fluid.

The antigenic peptide specifically binds to the antigen-specific T cells and labels them with the antigenic peptide-loaded complex. Antigenic peptide/MHC complexes can be, but need not be, conjugated to a reporter group, such as a radiolabel or fluorescent label, to facilitate detection. The molecular complex can be in solution or can be affixed to a solid substrate, such as a glass or plastic slide or tissue culture plate or latex, polyvinylchloride, or polystyrene beads.

Antigen-specific T cells which are bound to the antigenic peptides can be separated from cells which are not bound. Any method known in the art can be used to achieve this separation, including plasmapheresis, flow cytometry, or differential centrifugation. Antigen-specific T cells which have been isolated from a patient can be treated with a reagent, such as a cytokine, a chemotherapeutic agent, or an antibody, and reinfused into the patient to provide a therapeutic effect.

Optionally, the number of antigen-specific T cells which are bound to the antigenic peptides can be quantitated or counted, for example by flow cytometry.

Molecular complexes in which TCR polypeptides form ligand binding sites can also be used to label specific peptide/MHC complexes in vitro and in vivo. A distinct advantage of soluble high affinity TCR/Ig molecular complexes is that even in the absence of any a priori knowledge about their ligands, they can be useful in defining specific peptide/MHC ligands recognized, for example, by uncharacterized tumor-specific T cells or T cells involved in autoimmune responses. Not only are soluble divalent TCR/Ig molecules efficient probes for the qualitative and quantitative detection of specific peptide/MHC complexes, but due to their strong affinity for the target peptide, these molecular complexes can be used to purify and characterize specific peptide/MHC complexes.

The MHC molecules in peptide/MHC complexes can be MHC class I or class II molecules, or a non-classical MHC-like molecule. A peptide of a peptide/MHC complex can be, for example, a peptide which is expressed by a tumor, a peptide of an infectious agent, an autoimmune antigen, an antigen which stimulates an allelic response, or a transplant antigen or alloantigen.

A sample, such as a peripheral blood, lymphatic fluid, or a tumor sample, which comprises a peptide/MHC complex can be contacted with a composition comprising a molecular complex. The molecular complex comprises at least four fusion proteins. Two first fusion proteins comprise an immunoglobulin heavy chain and an extracellular domain of a TCR α chain. Two second fusion proteins comprise an immunoglobulin light chain and an extracellular domain of a TCR β chain. The fusion proteins associate to form a molecular complex. The molecular complex comprises two ligand binding sites. Each ligand binding site is formed by the extracellular domains of the TCR α and TCR β chains. The ligand binding site specifically binds to and labels the peptide/MHC complex and can be detected as described above.

Molecular complexes of the invention can also be used to activate or inhibit antigen-specific T cells. It is possible to conjugate toxin molecules, such as ricin or *Pseudomonas* toxin, to molecular complexes of the invention. Similarly, molecular complexes can be conjugated to molecules which stimulate an immune response, such as lymphokines or other effector molecules. Doses of the molecular complex can be modified to either activate or inhibit antigen-specific T cells.

A sample which comprises antigen-specific T cells can be contacted, in vivo or in vitro, with molecular complexes in which each ligand binding site is bound to an antigenic peptide. The antigenic peptide specifically binds to and activates or inhibits the antigen-specific T cells. For example, cytokine activation or inhibition can be stimulated or suppressed in specific T-cell subsets. Hewitt et al., *J. Exp. Med.* 175:1493 (1992); Choi et al. *Proc. Natl. Acad. Sci.* 86:8941 (1989); Kappler et al., *Science* 244:811 (1989); Minasi et al., *J. Exp. Med.* 177:1451 (1993); Sundstedt et al., *Immunology* 82:117 (1994); and White et al., *Cell* 56:27 (1989).

Molecular complexes of the invention can be used therapeutically, to inhibit or stimulate immune responses. For example, molecular complexes comprising antigenic peptides to which a patient has an allergic response can be administered to the patient in order to treat an allergy. The molecular complexes are administered to the patient at a dose sufficient to suppress or reduce a T cell response associated with the allergy.

Similarly, a patient who has received or will receive an organ transplant can be treated with molecular complexes of the invention. Molecular complexes in which each ligand binding site is bound to an alloantigen can be administered to a patient at a dose sufficient to suppress or reduce an immune response to the organ transplant. Alloantigens include the HLA antigens, including class I and class II MHC molecules, and minor histocompatibility antigens such as the ABO blood group antigens, autoantigens on T and B cells, and monocyte/endothelial cell antigens.

Autoimmune diseases, such as Goodpasture's syndrome, multiple sclerosis, Graves' disease, myasthenia gravis, systemic lupus erythematosus, insulin-dependent diabetes melitis, rheumatoid arthritis, pemphigus vulgaris, Addison's disease, dermatitis herpetiformis, celiac disease, and Hashimoto's thyroiditis, can be similarly treated. A patient who suffers from an autoimmune disease can be treated with molecular complexes of the invention in which each ligand binding site is bound to an antigenic peptide to which the patient expresses an autoimmune response. The molecular complexes are administered to the patient at a dose sufficient to suppress or reduce the autoimmune response.

Immune responses of a patient can also be induced or enhanced using molecular complexes of the invention. Molecular complexes in which each ligand binding site is bound to a peptide expressed by a tumor can be used to treat the tumor. The peptide can be a tumor-specific peptide, such as EGFRvBI, Ras, or p185$^{HER2}$, or can be a peptide which is expressed both by the tumor and by the corresponding normal tissue. Similarly, molecular complexes in which each ligand binding site is bound to a peptide of an infectious agent, such as a protein component of a bacterium or virus, can be used to treat infections. In each case, the appropriate molecular complexes are administered to the patient at a dose sufficient to induce or enhance an immune response to the tumor or the infection.

Molecular complexes of the invention can be bound to the surface of a cell, such as a dendritic cell. A population of molecular complexes in which all ligand binding sites are bound to identical antigenic peptides can also be bound to the cell. Binding can be accomplished by providing the fusion protein of the molecular complex with an amino acid sequence which will anchor it to the cell membrane and expressing the fusion protein in the cell or can be accomplished chemically, as is known in the art.

Compositions comprising molecular complexes of the invention can comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates—Compositions of the invention can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for a composition of the invention.

The particular dosages of divalent and multivalent molecular complexes employed for a particular method of treatment will vary according to the condition being treated, the binding affinity of the particular reagent for its target, the extent of disease progression, etc. However, the dosage of molecular complexes will generally fall in the range of 1 pg/kg to 100 mg/kg of body weight per day. Where the active ingredient of the pharmaceutical composition is a polynucleotide encoding fusion proteins of a molecular complex, dosage will generally range from 1 nM to 50 µM per kg of body weight.

The amounts of each active agent included in the compositions employed in the examples described herein provide general guidance of the range of each component to be utilized by the practitioner upon optimizing the method of the present invention for practice either in vitro or in vivo. Moreover, such ranges by no means preclude use of a higher r lower amount of a component, as might be warranted in a particular application. For example, the actual dose and schedule may vary depending on whether the compositions are administered in combination with other pharmaceutical compositions, or depending on individual differences in pharmacokinetics, drug disposition, and metabolism. Similarly, amounts may vary for in vitro applications depending on the particular cell line utilized, e.g., the ability of the plasmid employed to replicate in that cell line. For example, the amount of nucleic acid to be added per cell or treatment will likely vary with the length and stability of the nucleic acid, as well as the nature of the sequence, and may be altered due to factors not inherent to the method of the present invention, e.g., the cost associated with synthesis, for instance. One skilled in the art can easily make any necessary adjustments in accordance with the necessities of the particular situation.

A sufficient dose of the composition for a particular use is that which will produce the desired effect in a host. This effect can be monitored using several end-points known to those skilled in the art. For example, one desired effect might comprise effective nucleic acid transfer to a host cell. Such transfer could be monitored in terms of a therapeutic effect; e.g., alleviation of some symptom associated with the disease being treated, or further evidence of the transferred gene or expression of the gene within the host, e.g, using PCR, Northern or Southern hybridization techniques, or transcription assays to detect the nucleic acid in host cells, or using immunoblot analysis, antibody-mediated detection, or the assays described in the examples below, to detect protein or polypeptide encoded by the transferred nucleic acid, or impacted level or function due to such transfer.

The following are provided for exemplification purposes only and are not intended to limit the scope of the invention described in broad terms above.

MATERIALS AND METHODS

The following materials and methods are used in the examples described below.

*Cells and Culture Conditions*. RMA-S, RMA-S $L^d$, T2, T2 $K^b$, T2 Kbm3, T2 $K^{bm11}$, and RENCA cells were maintained by 1:10 passage three times weekly in RPMI-1640, supplemented with 2 mM glutamine, nonessential amino acids, 50 µg/ml of gentamicin, 5×M 2-mercaptoethanol, and 10% fetal calf serum.

T2, T2 $L^d$, and T cell hybridomas 5KC and DO11.10 were maintained by 1:20 passage three times weekly in RPMI-1640 supplemented with 2 mM glutamine, nonessential amino acids, 50 µg/ml of gentamicin, 5×10$^{-5}$ M 2-mercaptoethanol, and 10% fetal calf serum. Transfected T2 $L^d$ cells were grown in G418 (1 mg/ml, GIBCO).

Construction of the Soluble Divalent Molecules. The genes encoding the chimeric 2C TCR/Ig-molecule were constructed by insertion of cDNA encoding the extracellular domains of the TCR α and β chains upstream of cDNA encoding the murine IgG1 heavy, 93G7, and light chain, 91A3, respectively (FIG. 1A) (20). A HindIII restriction enzyme site and linker were inserted immediately 5' of the codon for Asp at the start of the mature kappa protein in clone 91A3. A KpnI restriction enzyme site was introduced 3' of the stop codon in the kappa polypeptide. A KpnI restriction site and linker were inserted immediately 5' of the codon for Glu located at the start of the mature Igγ$_1$ polypeptide in clone 93G7. An SphI restriction site was introduced 3' to the stop codon in the γ$_1$ polypeptide.

Figure 1B:
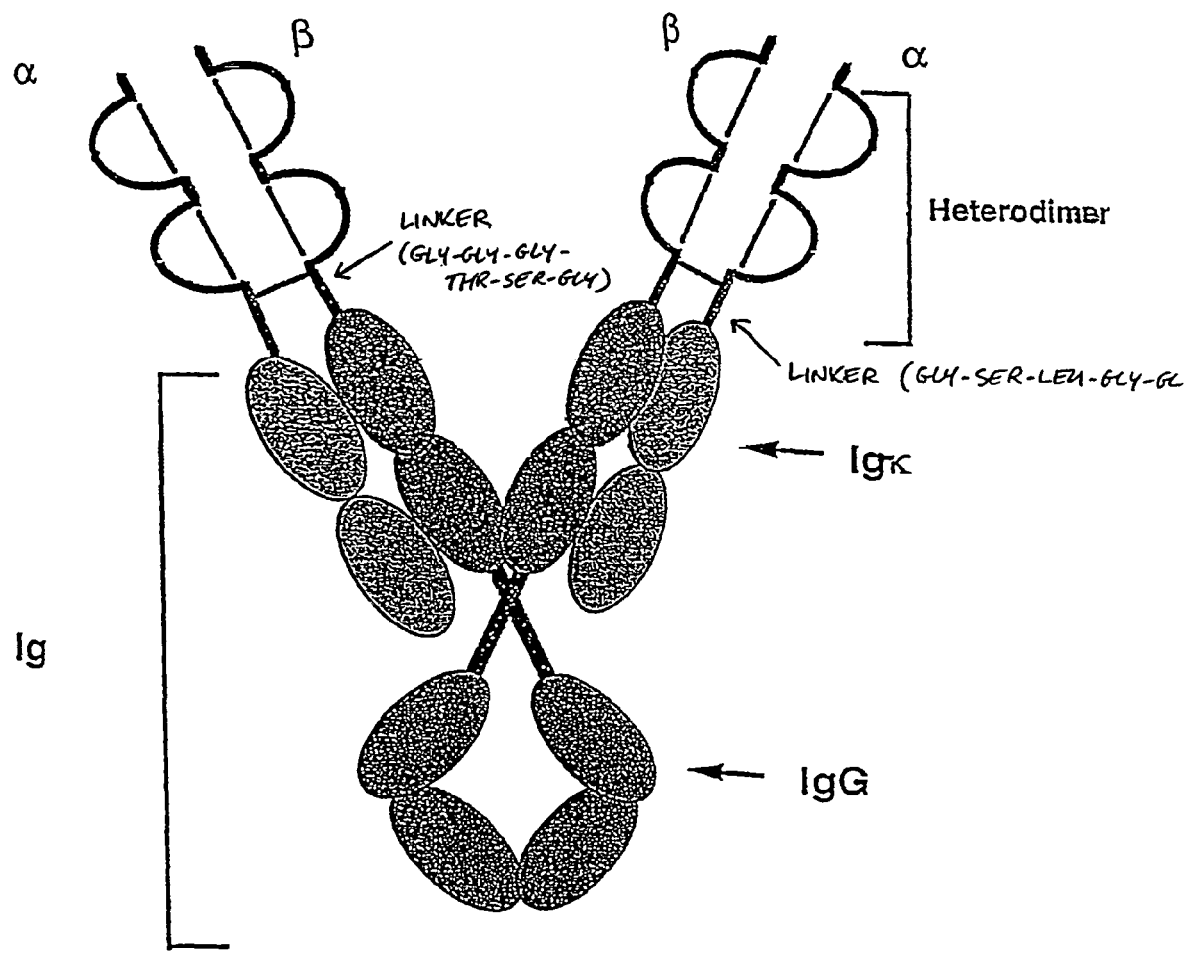
FIG. 1B. Heterodimeric transmembrane protein made divalent and soluble by covalent linkage of outer-membrane region to antibody.
Figure 1C:
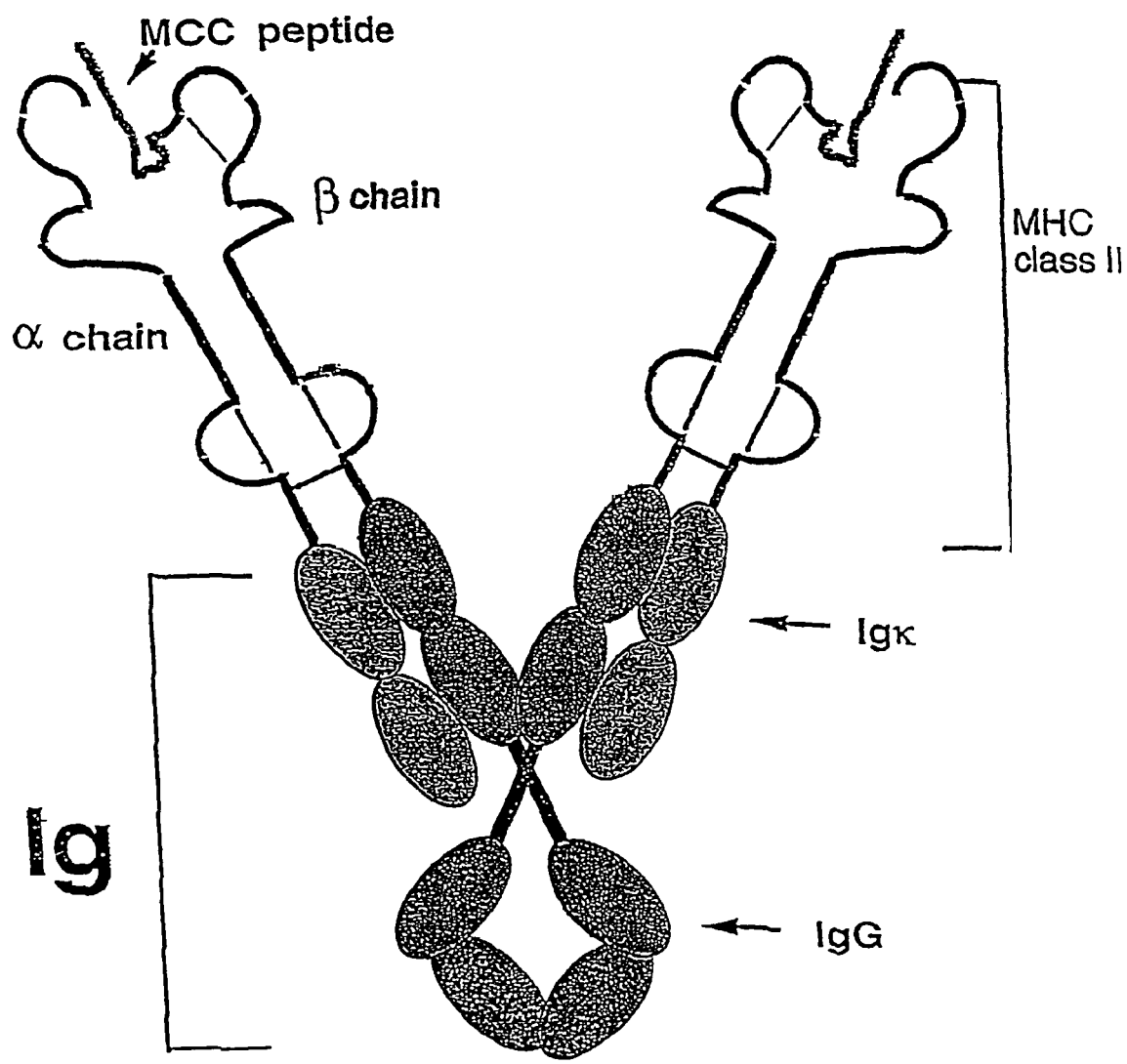
FIG. 1C. Outer-membrane region of MHC class II covalently linked to an antibody.
Figure 1D:
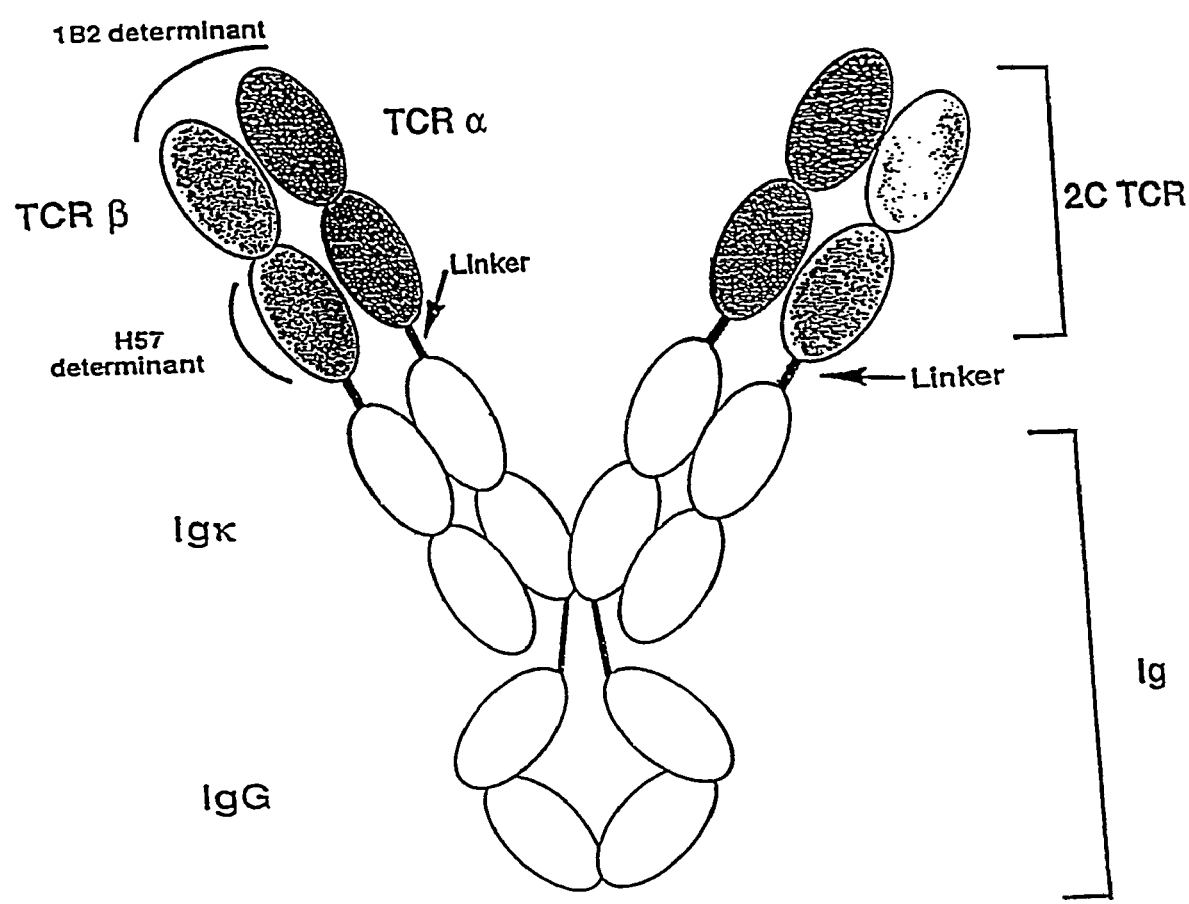
FIG. 1D. A schematic of the chimeric protein showing the TCR α polypeptide (shaded) linked to IgG1 heavy chain and TCR β polypeptide (shaded) linked to Ig kappa light chain is shown. The linkers between the chimeric chains consist of short glycine/serine spacers. Presumptive binding sites of two monoclonal antibodies (mAb), H57 (TCR specific) and 1B2 (2C TCR specific), on the putative 2C TCR/Ig structure are also noted.

The genes-encoding the 2C-TCR α and β chains have previously been described (5). A KpnI restriction site and linker were inserted immediately 3' to the codon for the Gln residue at the interface between the extracellular and transmembrane domains of the 2C-TCR α polypeptide. The 5' regions of the gene already expressed an appropriate restriction enzyme endonuclease site, EcoR1. An Xho1 site was introduced 5' to the start of the signal sequence in the 2C-TCR β chain, and a HindIII restriction enzyme endonuclease site was introduced immediately 3' to the codon for the Ile residue at the interface between the extracellular and transmembrane domains of the β polypeptide. In the construction of the chimeric proteins, linkers of six amino acid residues were introduced at the junctions between the end of the TCR α and β and the mature gamma and kappa polypeptides, respectively (FIG. 1B).

A similar approach was used to modify the genes encoding the I-E α and β chains. A KpnI restriction site and linker was inserted immediately 3' to the interface between the extracellular and transmembrane domains of the I-E β polypeptide. The 5' regions of the gene had already been modified to encode the MCC peptide (21) and also already expressed an EcoRI site. The I-E α chain was modified by introduction of a HindIII restriction enzyme endonuclease site immediately 3' to the codon at the interface between the extracellular and transmembrane domains.

A baculovirus expression vector was used, as described previously (21). This vector has two separate viral promoters, polyhedron and P10, allowing simultaneous expression of both chimeric polypeptide chains in the same cell (FIG. 1A). The expression vector was digested with XhoI and Kpn1 and 2C TCR$_β$/Ig$_{ic}$ was inserted downstream of the P10 promoter (FIG. 1A). Subsequently, the 2C TCRJIgyl was inserted into an EcoRI/SphI site downstream of the polyhedron promoter.

Mutagenesis. For mutagenesis, cDNA molecules'encoding the individual polypeptides were subcloned into pSP72 and pSP73 vectors (Promega, Madison, Wis.). Oligonucleotide-directed mutagenesis was performed using the Chameleon kit (Stratagene, La Jolla, Calif.). All mutations were confirmed by sequencing.

The following oligonucleotides were used to introduce the above mutations:
5' IgG1 mutation, ctgtcagtaactgcaggtgtccactctggtaccagcggtgaggttcagcttcagcagtctggagc (SEQ D3 NO:1);
3' IgG1 mutation, agcctctcccactctcctggtaaatgagcatgctctcagtgtccttggagccctctggtc (SEQ ID NO:2);
5' Igk mutation, ctgttgctctgttttcaaggtaccaggtgtggagcttagggaggatctgatatccagatgacgcaaa tccatcc (SEQ ID NO:3);
3' Igk mutation, gtcaagagatcaacaggaatgagtgttagggtaccagacaaaggtcctgagacgccaccaccagc (SEQ ID NO:4);
3' 2C TCR a mutation, cagatatgaacctaa actttcaaggaggaggtacctgtcagttatgggactccgaatc (SEQ ID NO:5);
5' 2C TCR β mutation, ccaaagagaccagtatcctgactcgaggaagcatgtctaacactgccttc (SEQ ID NO:6);
3' 2C TCRb mutation, ctgcaaccatcctctatgagatcggaagcttaggatctggtacctactggggaaggcc accctatatgc (SEQ ID NO:7);

3' IE$^d$α ggtagcgaccggcgctcagctggaattcaagcttccattctctttagtttctgggaggagggt-3' (SEQ ID NO:8);
IE$^k$b gcacagtccacatctgcacagaacaagggaggagggaggaggatccggttattagtacatttattaag (SEQ ID NO:9).

Detection and biochemical analysis of chimeras. The conformational integrity of the chimeric molecules was detected by ELISA assays using antibodies specific for each moiety of the protein. The primary antibody used was specific for murine IgG1 Fc. The secondary antibody used was either a biotinylated: H57 (used at 1:5,000 final dilution), a hamster monoclonal antibody (mAb) specific for a conformational epitope expressed on the 13 chain of murine TCR (22) or 1B2 (23, 24), a murine mAb specific for a clonotypic epitope expressed on 2C TCR. I-E$^k$/Ig was assayed using biotinylated 14.4.4, an anti I-E$_c$, chain specific mAb, as the secondary antibody.

Wells were incubated with the primary antibody, 10 mg/ml, for 1 hour at RT, and then blocked with a 2% BSA solution prior to use. After three washes with PBS containing 0.05% Tween 20 and 1% FCS, culture supernatants (100 µl) from infected baculovirus cells were incubated for 1 hour at RT. Plates were then washed extensively and incubated with the biotinylated second antibody. When using biotinylated second antibody 1B2, wells were incubated with 100 µl 10% mouse serum for an additional hour, after washing out unbound culture supernatants to reduce background reactivity.

After an hour incubation with the biotinylated antibody, the plates were washed and incubated with HRP-conjugated strepavidin (100 ml of a 1:10000 dilution) for one hour, washed and developed with 3,3',5,5'-tetramethylbenzidine dihydrochloride (TMB) substrate for 3-5 minutes. The reaction was stopped by the addition of 1M H$_2$SO$_4$ and optical density was measured at 450 nm. The assay was linear over the range of 1-50 ng/ml of purified IgG. I-E$^k$/Ig was assayed similarly with 14.4.4 as the primary antibody and goat-anti-mouse-lambda conjugated to horse radish peroxidase as the secondary antibody.

Purification of Chimeras. For protein production, *Trichoplusia ni* cells were infected with virus, MOI 5-10, and supernatants were harvested after 72 hours of infection. The chimeric protein was purified from one liter culture supernatants passed over a 2.5 ml affinity column of protein G sepharose. The chimeric protein was eluted with 0.1 M glycine/0.15 M NaCl, pH 2.4. The eluate was immediately neutralized with 2 M Tris pH 8 (0.1 M final concentration). Fractions were pooled, concentrated in an Amicon concentrator (50 kd molecular weight cutoff), and washed with PBS.

SDS PAGE analysis of the chimeric protein was preformed as described (25). Samples were electrophoresed through a 10% SDS-polyacrylamide gel.

Peptide Loading of Cells. RMA-S and T2 cell lines are defective in antigen processing and express functionally "empty" class I MHC on their cell surface. These "empty" MHC molecules can be loaded with peptides using the following protocol (25). Cells (RMA-S, RMA-S L$^d$, T2, T2 L$^d$, T2 Kb, T2 Kbm3 or T2 K$^{bm11}$) are cultured at 27° C. overnight. The following morning, cells are cultured in the presence of various antigenic peptides (100 µM final concentration) or in the absence of peptides for an additional 1.5 hours at 27° C. and then incubated for one hour at 37° C. RENCA cells were loaded with peptides by incubation with peptides (100 µM final concentration) for >2 hour at 37° C. Cells were then harvested and processed for FACS analysis as described.

All peptides were made by the Johns Hopkins University biopolymer laboratory peptide synthesis facility. Peptides were made by F-MOC chemical synthesis and then purified by preparative HPLC.

Measurement of affinities of soluble 2C TCR for H-2 $L^d$ molecules. Affinities of soluble 2C TCR analogs for peptide loaded cells were determined in a competition assay with FITC-30.5.7 Fab similar to one previously described. Schlueter et al., *Journal of Molecular Biology* 256:859-869 (1996). 30.5.7 is a monoclonal antibody that recognizes an epitope near the peptide-exposed face of H-2 $L^d$; thus 30.5.7 and 2C TCR compete for binding to the peptide exposed face of H-2 V. $K_d$ of 30.5.7 Fab for peptide-loaded RMA-S $L^d$ cells were determined as follows. Cells ($0.3 \times 10^6$/ml) were loaded with peptide as described above. Subsequently, peptide-loaded or control cells were incubated with varying concentrations of FITC-30.5.7 Fab for 1 hr. at 4° C., and then diluted 1:6 with FACS wash buffer (PBS, 1% FCS, 0.02% $NaN_3$) immediately prior to analysis by flow cytometry. $K_d$ were estimated from a plot of 1/(mean channel fluorescence) vs. 1/[FITC-30.5.7 Fab].

Affinities of 2C TCR analogs were determined by competition with constant concentrations of FITC-30.5.7 Fab. Cells were loaded with peptide, and subsequently incubated with a constant concentration of FITC-30.5.7 Fab and varying concentration of 2C TCR analogs for 1 hour at 4° C. Cells were diluted 1:6 with FACS wash buffer immediately prior to analysis by flow cytometry. Maximal inhibition of FITC-30.5.7 Fab binding was determined by incubation in the presence of 30.5.7 mAb (75 mg). $K_{app}$ was determined from a plot of 1/(% maximal inhibition) vs. [2C TCR analog]. $K_{app}$ was corrected for the affinity of FITC-30.5.7 Fab for peptide loaded cells according to the equation $K_d$, TCR=$K_{app}$/(1+ ([FITC 30.5.7 Fab]/$K_d$,30.5.7)) Schlueter et al., supra.

Direct Flow Microfluorimetry. Approximately $1 \times 10^6$ peptide-loaded or control cells were incubated for 60 minutes at 4° C. with either 100 µl of mAb 30.5.7 culture supernatants, or 50 µl of TCR/Ig culture supernatants, 10 µg/ml final concentration. Cells were washed twice in PBS and then incubated for an additional 60 minutes at 4° C. in 50 µl of 1:40 dilution of fluorescent phycoerythrin-labelled-F(ab')$_2$ goat anti-mouse IgG (Cappel Laboratories). Cells were then washed two additional times with FACS wash buffer prior to analysis by flow cytometry.

To compare level of fluorescence of cells stained with either the soluble divalent 2C TCR/Ig or the soluble monovalent 2C TCR, RMA-S $L^d$ cells were incubated with peptides, as described above. Cells were incubated for one hour with serial two-fold dilution of either soluble 2C TCR/Ig or soluble monovalent 2C TCR, washed once in FACS wash buffer, and then stained with saturating amounts of H57-FITC for an hour, washed twice in FACS wash buffer, and analyzed by flow cytometry.

For staining of MCC specific hybridoma cells, $^{MCC}IE^K$/Ig (5 µg/well) was incubated with cells for 1 hour at 4° C., washed and followed by goat anti-mouse $IgG_1$ conjugated to RPE for an additional hour. Hybridoma cells were then washed twice. Cells were analyzed by flow cytometry.

T cell stimulation assay. Various concentrations of soluble $^{MCC}IE^k{}_2$Ig or the murine anti-CD3 monoclonal antibody, 2C22, were immobilized on sterile Immunlon 4 plates (Dynatech) overnight at 4° C. Following two washes, either the MCC-specific 5KC cells or the control ovalbumin specific-DO11.10 cells ($1 \times 10^5$/well) were added in 250 µl of culture medium and incubated overnight at 37° C. IL-2 was measured using an ELISA assay.

CTL Assays. Splenocytes from 2C TCR transgenic mice (Sha et al. *Nature* 336:73-76, 1988) were resuspended at $1.25 \times 10^6$ per ml and stimulated with $1.75 \times 10^6$ BALB/c splenocytes that had been exposed to 3,000 cGy radiation. On day 7, the 2C T cell-enriched cultures were restimulated at $5 \times 10^5$ per ml with $2.5 \times 10^6$ per ml BALB/c splenocytes. Experiments were performed on this and subsequent stimulationUs on day 4. All subsequent stimulation was performed with $3.75 \times 10^5$ per ml 2C splenocytes and $2.5 \times 10^6$ per ml BALB/c cells in the presence of IL-2 (5 units/ml).

Assays were performed in triplicate according to established CTL protocols. Briefly, target cells ($2-4 \times 10^6$) were incubated with 100 5Ci $^{51}$[Cr] at 37° C. for 1 h. After three washes, cells were added to V-bottom 96 well plates ($3 \times 10^3$/100 µl) and incubated (25° C. for 1.5 hour) with peptides at the indicated concentrations. 2C T-cells ($3 \times 10^4$/100 µl) were added to targets and plates were incubated at 37° C. for 4.5 hour. Maximum release was achieved by incubating targets with 5% Triton X 100. Percent specific lysis was calculated from raw data using [(experimental release–spontaneous release)/(maximum release–spontaneous release)]×100.

Example 1

This example demonstrates general construction and biochemical characterization of chimeric molecules.

Characteristics of a general system for the expression of soluble divalent analogs of heterodimeric proteins include relative simplicity, broad applicability, and maintenance of molecular stability of the soluble analog. To accomplish this, IgG was chosen as a general molecular scaffold because it is divalent by nature and can be simply modified to serve as a scaffold (16, 26-28). Of further advantage is the fact that the IgG scaffold facilitates subunit pairing, folding, secretion, and stability of the covalently linked heterodimeric polypeptides.

Figure 2:
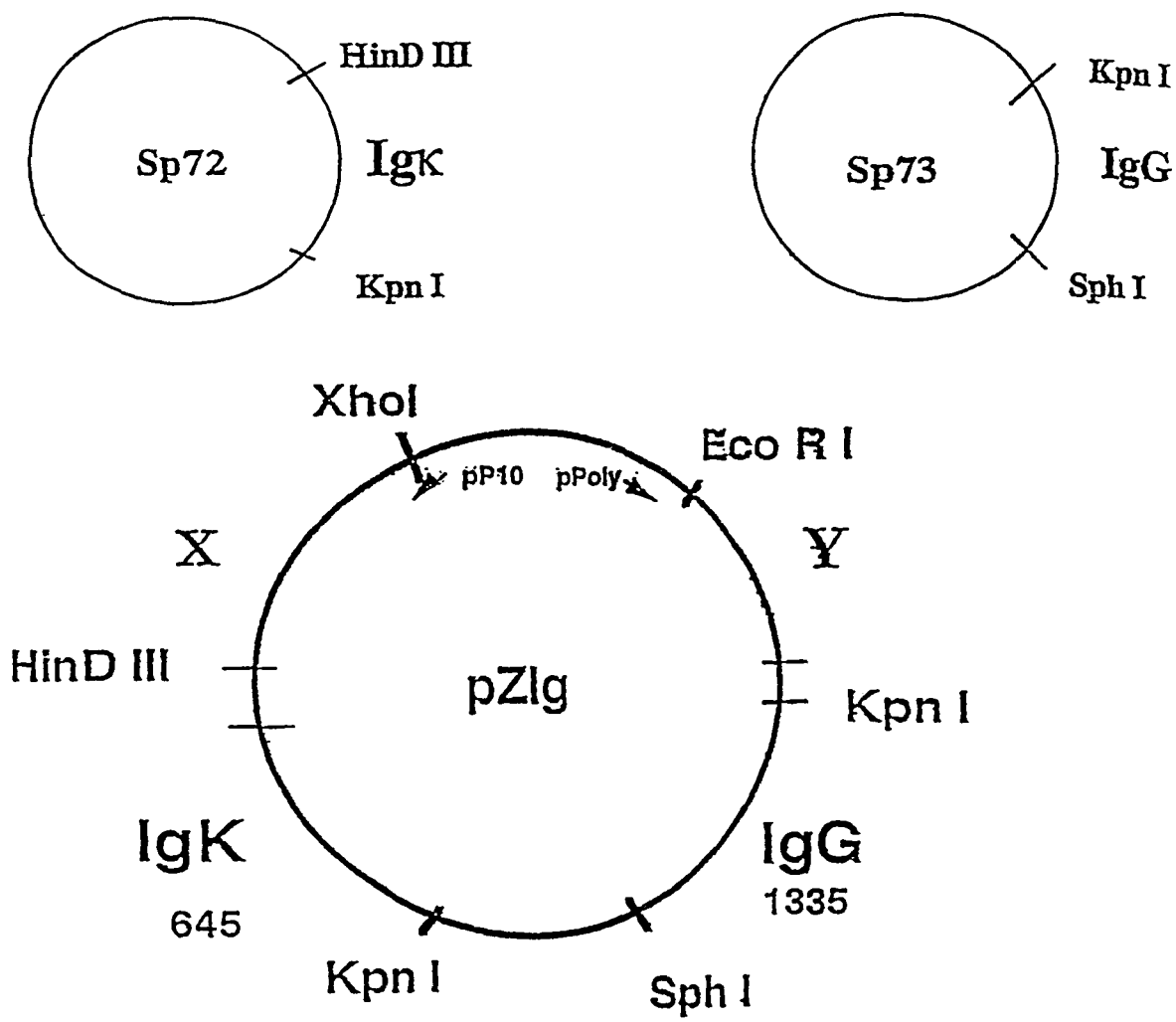
FIG. 2. Map of the expression vector, which encodes soluble divalent heterodimeric proteins. Multi-step construction schematic is shown to depict fusion of α and β polypeptide subunit linked to Ig heavy and light chains to form the chimeric Immunoglobulin molecules.

Using immunoglobulin as a backbone, a general system has been designed for expression of soluble recombinant multivalent analogs of heterodimeric transmembrane proteins (FIGS. 1B-1D and FIG. 2). As shown in FIG. 2, site-directed mutagenesis was used to insert restriction enzyme sites, such as KpnI and Hind III, into the 5' region of the Ig heavy and light chains, respectively. The enzyme sites were introduced immediately after the leader sequence prior to the start of the mature protein encoding the intact variable domains. This strategy leads to a generic system for expression of chimeric polypeptides and serves as a foundation molecule for construction of soluble divalent analogs of two different classes of heterodimeric proteins. The different classes of heterodimeric transmembrane proteins, which contain α and β polymorphic integral membrane polypeptides that bind each other forming a functional unit involved in immune recognition, include, but are not limited to, proteins such as T cell receptors, and class II MHC molecules, integrins, and cytokine receptors.

A multi-step construction was used to genetically fuse α and β polypeptides to immunoglobulin heavy and light chains to form the chimeric IgG molecules. In one embodiment, chimeric fusion partners consisted of cDNA encoding a murine IgG1 arsenate-specific heavy chain, 93G7, and light chain, 91A3 (Haseman et al *Proc Natl Acad Sci USA* 87:3942-3946 (1990)). Both of these immunoglobulin polypeptides have been expressed and produce intact soluble intact IgG1 molecules in baculovirus infected cells. cDNA encoding the light chain clone 91A3 was modified by introduction of 5'HindIII site and linker immediately prior to position one amino acid residue, Asp, at the start of the mature protein. A KpnI restriction enzyme endonuclease site was introduced after the stop codon in the mature polypeptide. cDNA encoding the 93G7 clone was modified but introduction of a KpnI restriction enzyme endonuclease site immediately prior to 5' to amino acid residue position Glu located at the start of the mature protein, and an SpiII restriction enzyme endonuclease site 3' to the stop codon in the mature IgG1 protein.

In another embodiment, we analyzed the ability of the Ig scaffold to facilitate production of two classes of heterodimers, TCR α,β heterodimers, and class II α,β heterodimers. The TCR heterodimer was derived from the well characterized alloreactive, class I-specific 2C CTL clone (24, 29). The class II MHC heterodimer was derived from the murine class II molecule I-Ek that had previously been modified to also encode a nominal peptide antigen derived from moth cytochrome C (MCC) (21, 30).

Soluble divalent TCR chimeras were generated by linking cDNA encoding the extracellular domains of TCR α or β chains to cDNA encoding Igγ1 heavy and κ light chain polypeptides, respectively. Site-directed mutagenesis was used to introduce restriction endonuclease enzyme sites into the TCR α and β genes immediately preceding the regions encoding the transmembrane domains (FIG. 2). The enzyme sites introduced into the TCR cDNAs were complementary to those introduced into the immunoglobulin-cDNAs-5' to the regions encoding the intact immunoglobulin variable domains. The DNA encoding the restriction sites was part of a sequence encoding the six amino acid glycine, serine linker (FIG. 1B) which was designed to allow flexibility. The TCR α-Igγ and TCR β-Igκ constructs were cloned into the modified dual promoter baculovirus expression vector, pAcUW51 (FIG. 2) (21). This vector allows simultaneous expression of both chimeric chains from cells infected with a single viral stock.

For expression of soluble divalent class II MHC molecules, cDNAs encoding the I-Ek β and I-E α chains were genetically linked to cDNA encoding the Igγ1 heavy and κ light chain polypeptides, respectively. The 5' end of the β cDNA was previously linked via a thrombin cleavage site to DNA encoding an antigenic peptide derived from MCC (residues 81-101) (21). Site-directed mutagenesis was used to introduce restriction enzyme endonuclease sites into the 3' region of the $^{MCC}$I-Ekβ and I-Eα genes immediately preceding the regions encoding the transmembrane domains, as described for 2C TCR. The constructs were cloned into the dual promoter baculovirus expression vector described above.

FIG. 1B depicts a schematic, representation of a chimeric molecule. The α polypeptide is attached via a short six amino acid linker, GGGTSG (SEQ ID NO:10), to the amino terminal end of the variable region of the Igκ chain, while the β polypeptide is attached via another six amino acid linker, GSLGGS (SEQ ID NO:11), to the amino terminus of the variable region of the Igγ chain.

Example 2

This example demonstrates detection of soluble heterodimeric proteins.

Cells infected with baculovirus containing transfer vectors encoding the soluble chimeric Ig constructs described above secrete a soluble chimeric Ig-like molecule detected by specific ELISA assays 4-5 days post infection. For 2C TCR/IgG, the assay was based on a primary antibody specific for murine-IgG1 Fc (plated at 10 µg/ml) and a biotinylated secondary antibody, H57 (used at 1:5000 final dilution), specific for a conformational epitope expressed on the β chain of many TCR (FIG. 5A) or biotinylated 1B2 or a monoclonal antibody specific for a clontoypic epitope expressed on 2C TCR (FIG. 5B). For detection of 1-E/IgG chimeric molecules, the same primary antibody was used and the biotinylated secondary antibody was 14.4.4, which is specific for I-E a chain (FIG. 5C). Supernatants from infected cells were incubated for 1 hour at room temperature. Plates were washed extensively with phosphate buffered saline, incubated with the biotinylated secondary antibody for 1 hour at room temperature. The plates were then washed and incubated with HRP-conjugated strepatvidin (100 µl of a 1:10000 dilution) (Sigma, St. Louis, Mo.) for 1 hour at room temperature, washed and developed with 3,3',5,5'-tetramethylbenzidine dihydrochloride (TMB) substrate for 3-5 minutes. Supernatants from cells infected with baculovirus containing the 2C TCR/Ig and I-EAg transfer vectors were compared to control supernatant from cells infected with the wild type baculovirus.

Figure 5:
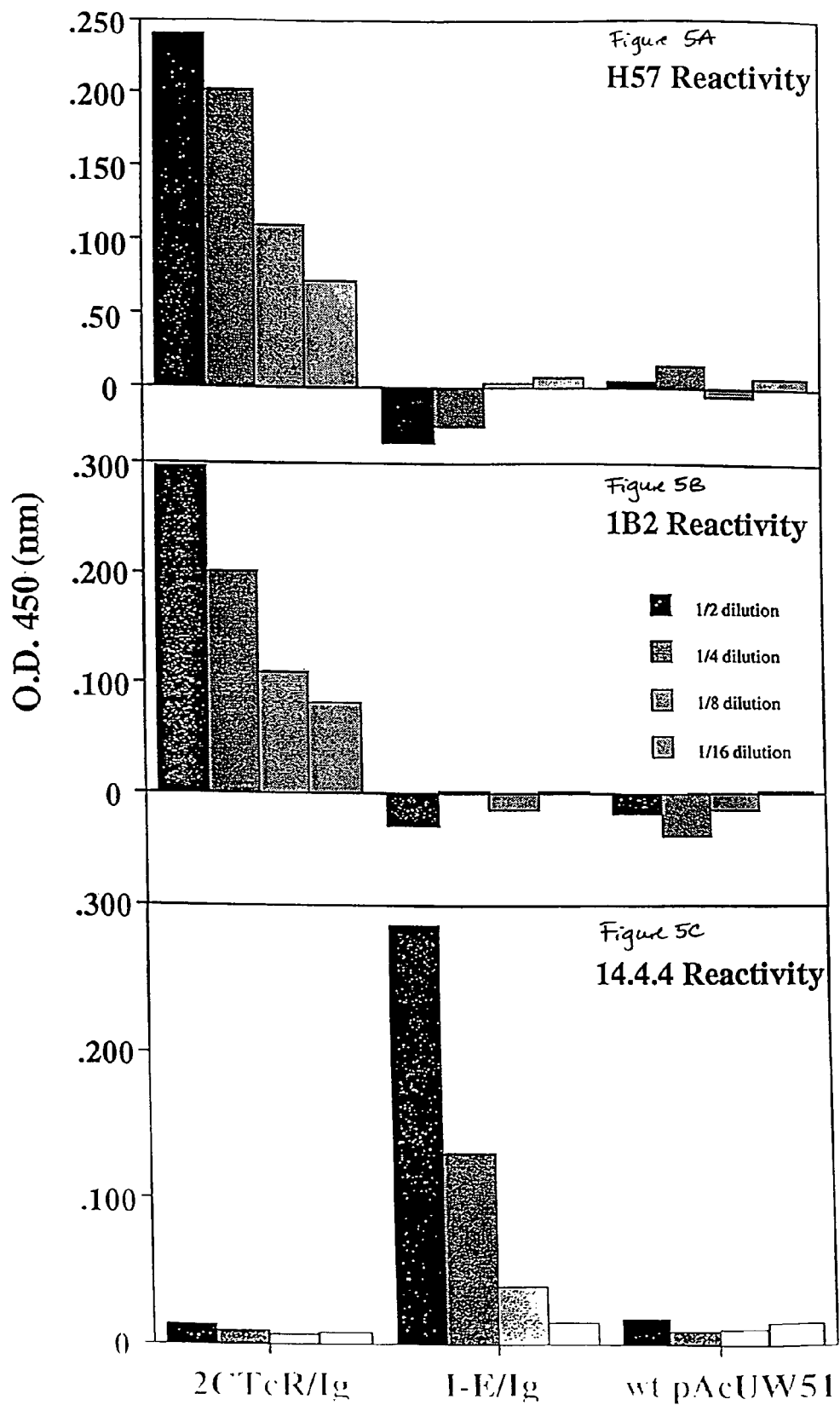
FIG. 5. Biochemical characterization of TCR, MHC/Ig. Detection of chimeras in baculovirus supernatants by ELISA assays. Plates were coated with goat-anti-mouse Fc. For detection of TCR/Ig, the secondary antibody was either biotinylated H57 (FIG. 5A) or the anti 2C mAb 1B2 (FIG. 5B), followed by streptavidin-HRP. For detecting I-E/Ig, the secondary antibody was biotinylated 14.4.4 (FIG. 5C).

The chimeric proteins are conformationally intact as shown in FIG. 5. The soluble divalent 2C TCR/Ig is reactive with H57, a monoclonal antibody specific for a conformational epitope expressed on most TCRβ chains as well as with 1B2, the anti-clonotypic monoclonal antibody determinant specific for the 2C TCR as shown in FIGS. 5A and 5B. Soluble divalent class II molecules are reactive with the conformationally dependent monoclonal antibody specific for a native alpha chain determinant only expressed on intact I-E molecules, monoclonal antibody 14.4.4 as shown in FIG. 5C. The immunoglobulin portion of the chimeric molecules is also conformationally intact. It is reactive in an immunoglobulin specific ELISA, as mentioned above, and can be used to purify the chimeric molecules. Protein G or arsenate-sepharose affinity purification column methods can also be used.

Figure 6:
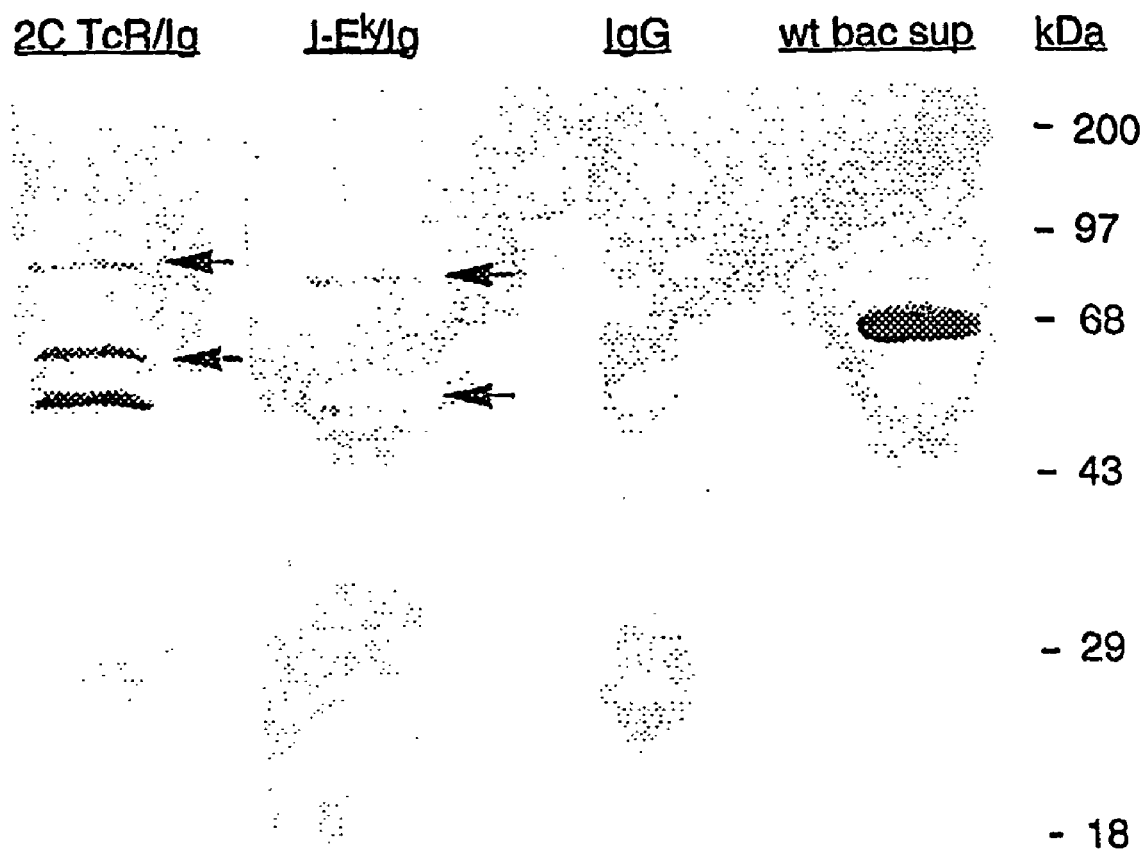
FIG. 6. A 10% SDS PAGE gel of affinity purified samples of I-$E^k$/Ig and 2C TCR/Ig chimeric proteins. Purified crude IgG and supernatant form *T. ni* cells infected with wild-type baculovirus are shown for comparison.

The purified material has the expected molecular weights when analyzed by SDA-PAGE as depicted in FIG. 6. The chimeric TCRβ/Igκ has an apparent molecular weight (MW) of 55,000 and the chimeric TCRα/Igγ1 has an apparent MW of approximately 89,000. The chimeric I-Eα/Igκ has an approximate MW of 44,000 and the chimeric I-Eβ/Igγ1 has an apparent MW of approximately 76,000.

Example 3

This example demonstrates affinity measurements of soluble divalent TCR interaction with peptide/MHC complexes.

A competitive inhibition assay was developed to measure the affinity of soluble 2C TCR/Ig for peptide/MHC complexes. This assay, similar to one previously used to determine the affinity of soluble monovalent 2C TCR for peptide MHC complexes (Schlueter et al., *Journal of Molecular Biology* 256:859-869 (1996), is based on mAb 30.5.7 binding to a region of the x2 helix of H-2 $L^d$ that overlaps with TCR receptor binding (Solheim et al., *Journal of Immunology* 154: 1188-1197 (1995); Solheim et al., *Journal of Immunology* 150:800-811 (1993).

Briefly, affinities of 30.5.7 Fab fragments for RMA-S $L^d$ cells were determined by direct saturation analysis of 30.5.7 Fab binding to cells analyzed by flow cytometry. Cells were incubated with increasing amounts of FITC labeled 30.5.7 Fab, and dissociation constants were estimated from a plot of 1/MCF vs. 1/[30.5.7 Fab]. Affinities of 2C TCR analogs were determined by competition of the 2C TCR analog with a constant amount of FITC labeled 30.5.7 Fab fragments for RMA-S $L^d$ cells as described above. $K_{app}$ was calculated from a plot of (% maximal 30.5.7 Fab binding)$^{-1}$ vs. [2C TCR analog]. The $K_{app}$ was corrected for the affinity of 30.5.7 Fab for RMA-S $L^d$ cells according to the equation $K_{d,TCR}=K_{app}/(1+\{30.5.7 \text{ Fab}\}'K_{d,30.5.7})$ (Schlueter et al., 1996). The values reported in the Table 2 are from one representative experiment that has been repeated at least three times. Each data point used in determination of the $K_d$ is the average of duplicate points. Hence, the affinity of soluble TCR analogs was measured in terms of their inhibition of 30.5.7 binding.

To determine the affinity of the soluble 2C TCR analogs, one has to first determine the $K_d$ of 30.5.7 Fab fragments for peptide-loaded H-2 $L^d$ molecules. This measurement was determined by direct saturation analysis of 30.5.7-FITC Fab binding to H-2 $L^d$ molecules on the surface of RMA-S $L^d$ cells. RMA-S cells were chosen because these cells express empty MHC molecules that can be readily loaded with specific peptides of interest (Catipovic et al., *Journal of Experimental Medicine* 176:1611-1618 (1992); Townsend et al., *Nature* 340:443-428 (1989). The affinity of 30.5.7 for H-2 $L^d$ molecules is dependent on the peptide loaded into H-2 $L^d$ (Table 2). The affinity of the 30.5.7 for QL9-loaded H-2 $L^d$ molecules is 12.2 nM while the affinities for p2Ca, pMCMV and SL9-loaded H-2 $L^d$ molecules range between 4.8-6.4 nM. These small, peptide-dependent, differences in affinity are reproducible and variations in affinity were accounted for in the competitive binding assays. These values are in good agreement with the previously measured affinities of 125I-30.5.7 Fab for the same peptide/H-2 $L^d$ complexes (8.8 to 16 nM; Schlueter et al., 1996).

Figure 7:
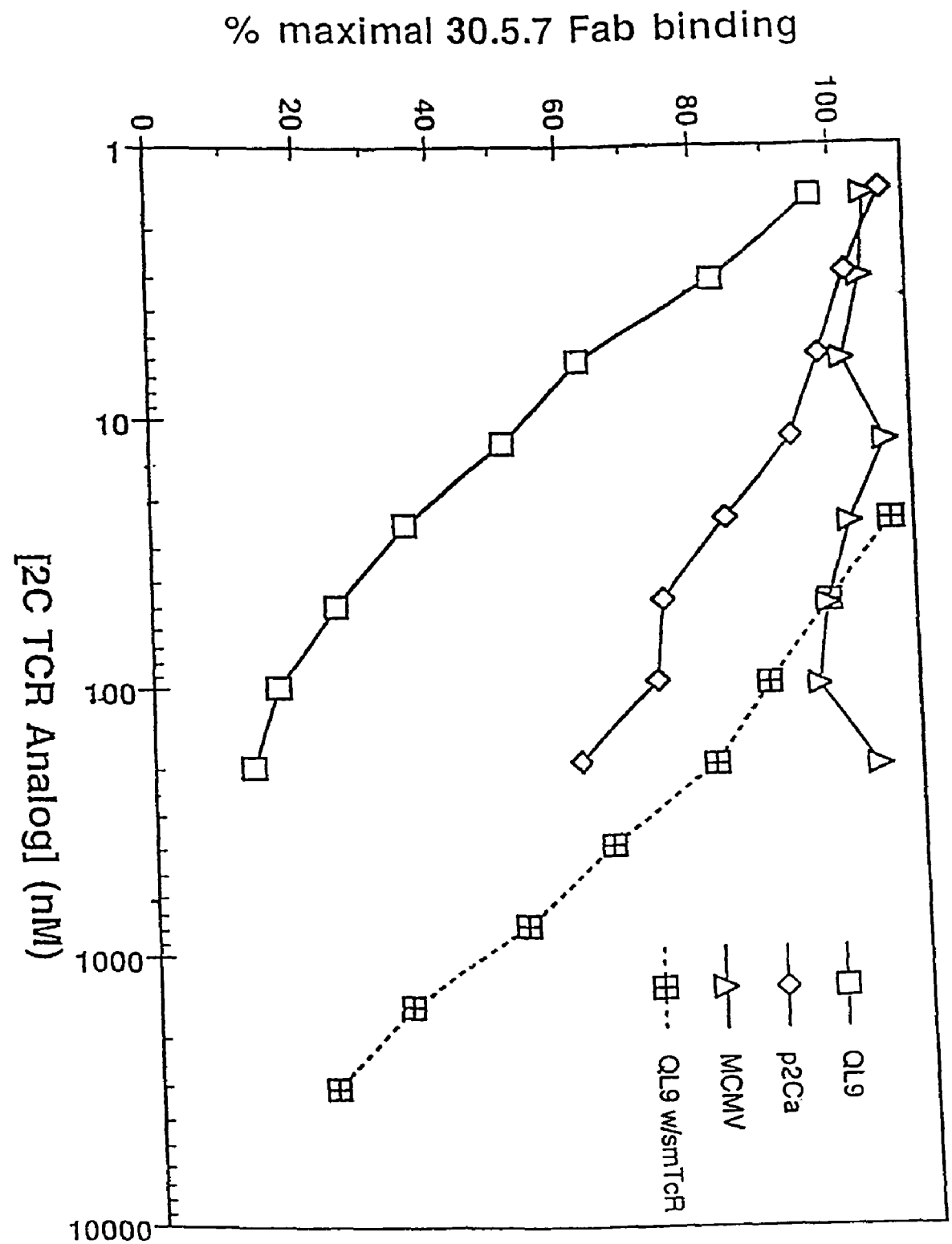
FIG. 7. Graph showing that the affinity of soluble divalent 2C TCR/Ig for peptide/H-2 $L^d$ complexes is higher than that of soluble monovalent 2C TCR. RMA S-$L^d$ cells were loaded with peptides (QL9, p2Ca, or pMCMV) and subsequently incubated with a constant amount of FITC-labeled 30.5.7 Fab and varying concentrations of either 2C TCR/Ig (solid lines) or soluble monovalent 2C TCR, sm2C TCR (dashed line). Binding of FITC-30.5.7 Fab was determined by flow cytometry. Results are plotted as the percent maximal (no 2C TCR Analog) 30.5.7 binding vs. the concentration of 2C TCR analog. Apparent affinities were determined from a replot of 1/(% maximal 30.5.7 binding) vs [TCR Analog] see text and Table II for further discussion. Data shown are from one representative experiment that has been repeated at least three times. Each data point is the average of duplicates.

2C TCR/Ig inhibited binding of 30.5.7 Fab to H-2 $L^d$ molecules loaded with either QL9 or p2Ca peptides, but did not inhibit 30.5.7 Fab binding to pMCMV loaded H-2 $L^d$ molecules (FIG. 7). The affinity of soluble divalent 2C TCR/Ig for QL9 loaded molecules is 13.3 nM (FIG. 7 and Table 2). As expected, the affinity of 2C TCR/Ig for p2Ca loaded molecules, 90 nM, is lower than that for QL9 loaded H-2 $L^d$. Although a small amount of competitive inhibition was seen with SL9 loaded cells, the affinity of the soluble divalent 2C TCR/Ig chimeras for SL9 loaded molecules is too low to be accurately measured under the conditions tested.

In all cases analyzed, the affinity of the soluble divalent 2C TCR/Ig was significantly higher than the affinity of the soluble monovalent 2C TCR for its cognate ligand (FIG. 7 and Table 2). The affinity of soluble divalent 2C TCR/Ig was 50-fold higher for QL9-loaded H-2 $L^d$ and at least 20-fold higher for p2Ca-loaded H-2 $L^d$ molecules than that of soluble monovalent 2C TCR for the same peptide/MHC complexes (Table 2). Thus, the affinity of soluble 2C TCR/Ig chimeras for cognate ligands was significantly increased. The finding that the chimeric molecules of the present invention demonstrate increased affinity for their specific ligands over what is seen for monovalent molecules was not an expected result. In fact, the chimeric CD4-IgG molecules disclosed in Capon et al., *Nature* 337:525-531 (1989), do not demonstrate improved target affinity.

TABLE 2

Measured Affinities of TCR analogs for peptide loaded RMA-SL$^d$ cells

| Peptide/MHC complex | 30.5.7 Fab $K_d$ (nM) | 2C TCR/Ig $K_{app}$ (nM) | 2C TCR/Ig $K_d$ (nM) | 2C-sm TCR $K_{app}$ (nM) | 2C-sm TCR $K_d$ (nM) |
|---|---|---|---|---|---|
| QL9 | 12.2 | 18.3 | 13.3 | 953.4 | 613.6 |
| p2Ca | 5.8 | 107.7 | 90.5 | >2000² | >2000² |
| pMCMV | 4.8 | ndc¹ | ndc¹ | —³ | —³ |

¹ndc - no detectable competition with 30.5.7 Fab fragments
²Competition was detected at the highest concentration of 2C-smTCR used, but an accurate measure of the $K_d$ could not be determined.
³not done.

Example 4

This example demonstrates binding specificity of soluble divalent TCR chimeras to peptide-loaded H-2 $L^d$ molecules.

Based on the relatively high affinity of soluble divalent 2C TCR/Ig for peptide/MHC complexes, we postulated that these molecules might be useful in analysis of peptide/MHC complexes by direct flow cytometry-based assays. To study peptide specificity of 2C TCR/Ig, we compared reactivity of 2C TCR/Ig with that of H-2 $L^d$ reactive mAb, 30.5.7, in direct flow cytometry assays. Specific peptides (see Table 3 for sequences) were loaded into H-2 $L^d$ molecules on RMA-S $L^d$ cells. Peptides listed in Table 2 are a collection of H-2 $L^d$ and H-2 $K^b$ binding peptides used in analysis of the reactivity of the soluble divalent 2C TCR/Ig. Lysis and affinity data are summarized from their primary references (Corr et al., *Science* 265:946-49, 1994; Huang et al., *Proc. Natl. Acad. Sci.* 93, 1996; Solheim et al., *J. Immunol.* 150:800-811, 1993; Sykulev et al., *Immunity* 1:15-24, 1994a; Sykulev et al., *Proc. Natl. Acad. Sci.* 91:11487-91, 1994b; Tallquist et al., *J. Immunol.* 155:2419-26, 1996; Udaka et al., *Cell* 69:989-98, 1996; Van Bleek and Nathanson, *Nature* 348:213-16, 1990).

TABLE 3

Peptides used in this study:
Their reported effectiveness in 2C CTL assays and affinities of 2C TCR for peptide/MHC complexes.

| peptide name | peptide sequence | MHC restriction | 2C-mediated lysis | $K_d$ (µM) |
|---|---|---|---|---|
| p2Ca | LSPFPFDL (SEQ ID NO: 12) | H-2 $L_d$ | +++ | 0.5-0.1 |
| QL9 | QLSPFPFDL (SEQ ID NO: 11) | H-2 $L_d$ | ++++ | 0.066 |
| SL9 | LSPFPFDLL (SEQ ID NO: 14) | H-2 $L_d$ | +/− | 71 |
| tum | TQNHRALDL (SEQ ID NO: 15) | H-2 $L_d$ | na | na |
| pMCMV | YPHFMPTNL (SEQ ID NO: 16) | H-2 $L_d$ | − | nd |
| gp 70 | SP SYVYHQF (SEQ ID NO: 17) | H-2 $L_d$ | na | na |
| dEV-8 | EQYKFYSV (SEQ ID NO: 18) | H-2 $K_b$ | − | unknown |
| dEV-8 | | H-2 $K_{bm3}$ | +++ | unknown |
| SIY | SIYRYYGL (SEQ ID NO: 19) | H-2 $K_b$ | +++ | unknown |
| SIY | | H-2 $K_{bm3}$ | unknown | unknown |
| pVSV NP(52-59) | RGYVYQGL (SEQ ID NO: 20) | H-2 $K_b$ | − | nd | na - not available.
nd - none detected. The affinity were below the sensitivity of the assay used.

Figure 8:
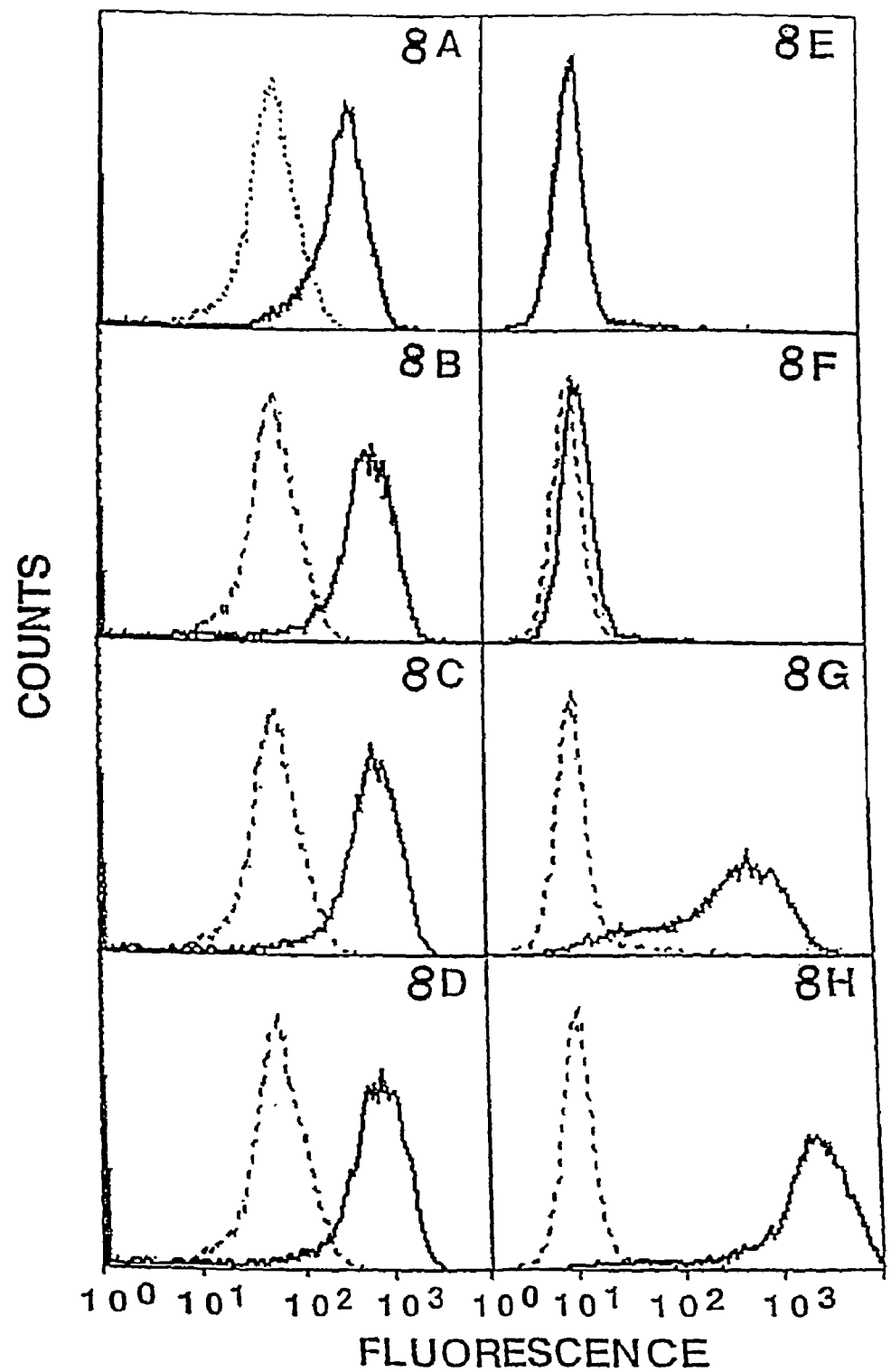
FIG. 8. Flow cytometry analysis of cells stained with either purified mAb, 30.5.7 (FIG. 8A-8D), or 2C TCR/Ig culture supernatants (FIGS. 8E-8H). In each panel the histogram of treated cells (solid line) is contrasted with that of cells not treated with any peptide and cultured for one hour at 37° C. (broken line). Histograms shown are from one representative experiment that has been repeated at least three times.

The temperature-dependent reactivity of RMA-S $L^d$ with 2C TCR/Ig was significantly different than the reactivity of RMA-S $L^d$ with mAb 30.5.7. As expected (Solheim et al., 1995; Solheim et al., 1993), RMA-S $L^d$ cells expressed more serologically reactive H-2 $L^d$ molecules recognized by mAb 30.5.7 on cells cultured at 27° C. than when cells were cultured at 37° C. (FIG. 8A); mean channel fluorescence (MCF) increased approximately 5-fold. Thus the epitope on H-2 $L^d$ molecules recognized by mAb 30.5.7 can be stabilized by incubating cells at low temperatures. In contrast, RMA-S $L^d$ cells expressed very low amounts of H-2 $L^d$ molecules recognized by 2C TCR/Ig on cells cultured at either 27° C. or at 37° C. (FIG. 8, Panel E). This finding is consistent with the expected peptide-dependent reactivity of 2C TCR/Ig which should not recognize unloaded MHC, even when conformationally stabilized by decreased temperature.

Figure 9:
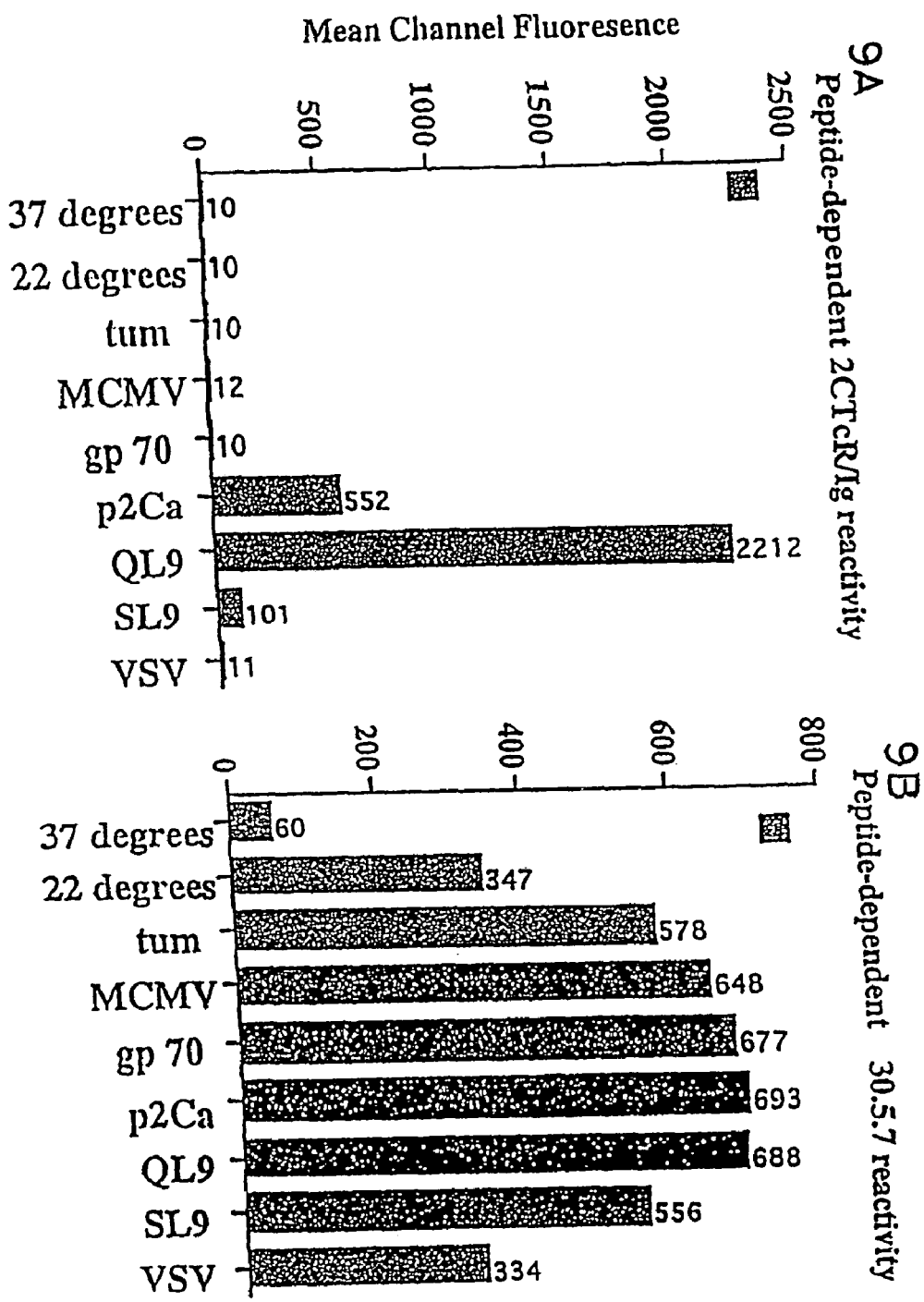
FIG. 9. Comparison of 2C TCR/Ig reactivity vs. mAb 30.5.7 reactivity in peptide-stabilized H-2 $L^d$ molecules. RMA-S $L^d$ cells were incubated under various conditions. Following overnight incubation of RMA-S $L^d$ cells at 27° C., cells were cultured in the presence or absence of various H-2 $L^d$ binding peptides: no peptide cells maintained at 27° C.; p2Ca, and QL9 were added to cultures as described in Materials and Methods, below.

2C TCR/Ig reactivity also showed exquisite peptide specificity. As expected, all H-2 $L^d$-binding peptides stabilized expression of the epitope recognized by mAb 30.5.7 (FIG. 8, Panels B-D and FIG. 9). Only H-2 $L^d$ molecules loaded with 2C reactive peptides, peptides p2Ca, QL9, and SL9 expressed peptide/H-20 epitopes that reacted with 2C TCR/Ig (FIG. 8, Panels F-H and FIG. 9). MCF increased approximately 10- to 200-fold, from a MCF of 10 for either unloaded cells or cells loaded with an irrelevant H-2 $L^d$ binding peptide, to as high as 2200 for RMA-S $L^d$ cells loaded with peptide QL9 (FIG. 9). The pattern of reactivity mimicked the known affinities of monovalent 2C TCR for peptide/H-2 $L^d$ complexes (see Table 3 for affinities). RMA-S $L^d$ cells loaded with peptide QL9, p2Ca, or SL9 had MCF values of 2200, 550, and 100, respectively, when stained with 2C TCR/Ig. Thus, soluble divalent 2C TCR/Ig chimeras reacted strongly with QL9/H-2 $L^d$ complexes, modestly with p2Ca/H-2 $L^d$ complexes, and weakly with SL9/H-2 $L^d$ complexes. The fact that 2C TCR/Ig bound to SL9-loaded H-2 $L^d$ molecules indicates, that even in a direct flow cytometry assay, soluble divalent 2C TCR/Ig chimeras could be used to detect specific peptide/MHC complexes that have affinities as weak as 71 µM for monovalent 2C TCR.

Example 5

This example demonstrates inhibition of in vitro 2C T cell mediated lysis by soluble divalent 2C TCR/Ig molecules.

Soluble divalent 2C TCR/Ig blocks 2C reactive T cell responses. Since soluble divalent 2C TCR/Ig interacts with high avidity with H-2 $L^d$ molecules loaded with the appropriate peptides in the flow cytometry assay, we explored whether the reagent could effectively inhibit 2C T cells in in vitro cytotoxicity CTL assays. This was analyzed using a cell line derived from 2C transgenic mice to lyse tumor target cells expressing H-2 $L^d$. CTL were tested in a routine 4 hour $^{51}$Cr cytotoxicity assay. Untransfected, MC57G, and $L^d$ transfected, MC57G $L^d$, cells were used as targets. The percent specific lysis was determined as: $^{51}$Cr cpm (experimental)-CPM (spontaneous)/cpm (maximum)-cpm (spontaneous). Standard errors were routinely less than 5% and spontaneous release was usually 10-15% of maximal release.

Figure 10:
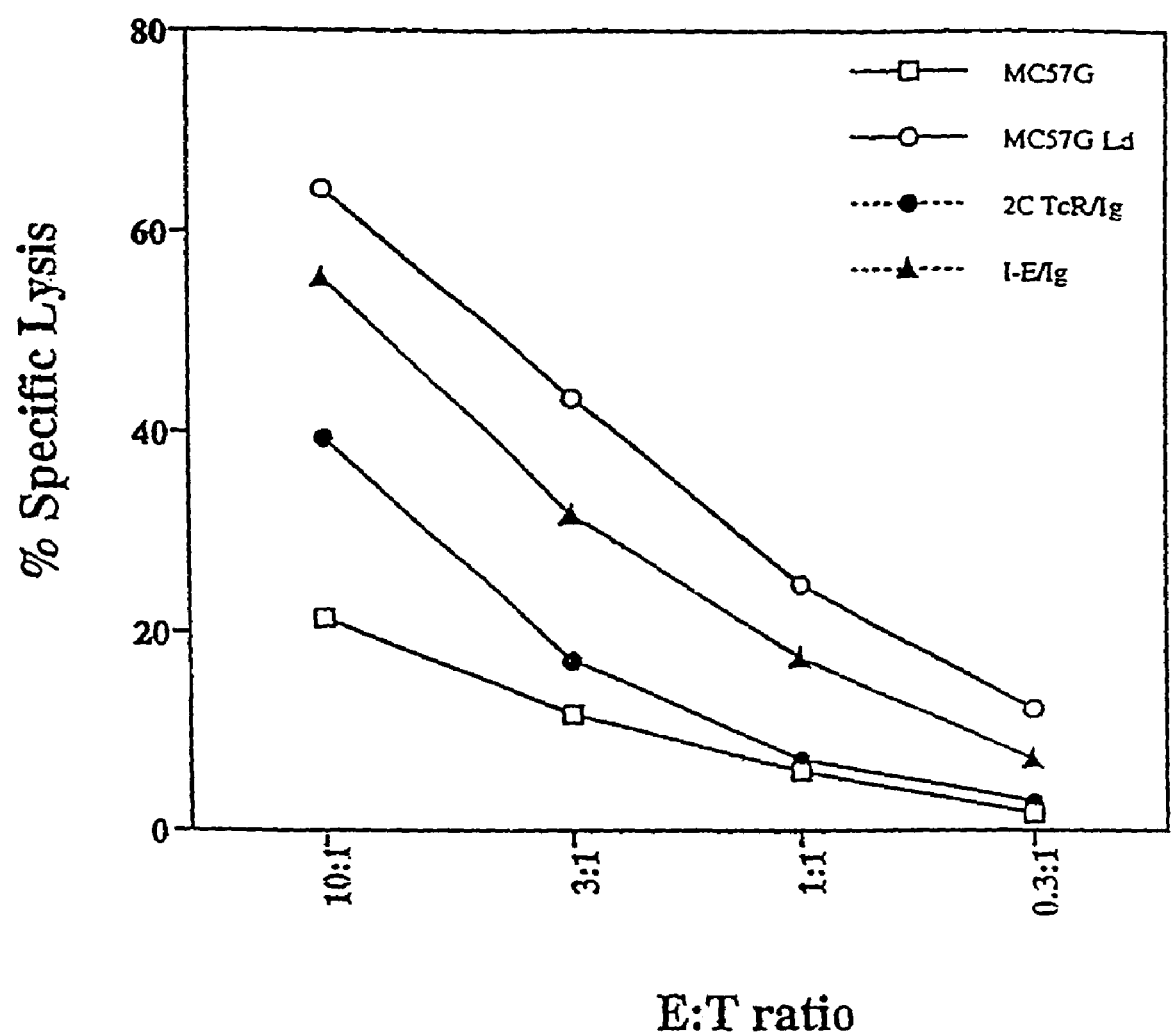
FIG. 10. Graph demonstrating inhibition of in vitro 2C T cell mediated lysis by soluble 2C TCR/Ig complexes.

Using both untransfected MC57G and $L^d$ transfected, MC57G $L^d$, we were able to establish a window of H-2$L^d$ specific lysis mediated by the 2C CTL line. To test the influence of 2C TCR/Ig, target cells were pretreated with either 2C TCR/Ig, or I-E$^k$/Ig and analyzed for lysis by the CTL cell line derived from 2C transgenic mice. Significant inhibition of lysis was seen at each effector to target cell ratio analyzed when cells were treated with 2C TCR/Ig (see FIG. 10). While some non-specific inhibition was seen in the I-E$^k$/Ig treated target cells, significantly more inhibition was seen in the 2C TCR/Ig treated target cells.

In this assay, the target cells were normal tumor cells which load their cell surface MHC molecules with a variety of different endogenous peptides. Using these target cells, one does not need to specifically load 11-2 $L^d$ molecules with the p2Ca peptide, since p2Ca or p2Ca-like peptides, together with a large number of irrelevant peptides, are endogenously loaded onto cellular MHC molecules. Inhibition of CTL-mediated lysis indicates that soluble divalent 2C TCR/Ig can effectively interact with the relevant peptides even within a milieu of a large number of irrelevant peptides. Thus, this approach could be used to search the universe of peptide/MHC complexes to identify only those complexes relevant to specific T cell responses of interest. In particular, these high avidity soluble analogs of heterodimeric proteins may specifically be useful in identification of unknown tumor and autoimmune antigens.

Example 6

This example demonstrates binding of soluble divalent TCR chimeras to self restricted peptide/MHC complexes.

In addition to recognizing peptide/H-2 $L^d$ ligands, two peptides, SIY and dEV-8, that sensitize either H-2 K$^b$ or H-2 K$^{bm3}$ targets for lysis by 2C CTL have also been defined (see Table 3 for sequences). To analyze the ability of 2C TCR/Ig to bind to these alternate 2C-reactive complexes, the binding of 2C TCR/Ig to peptide loaded transfected T2 cells was studied. Since T2 cells are derived from a human cell line, T2 cells do not naturally express H-2 K$^b$ as do RMA-S cells. Thus to study the binding of 2C TCR/Ig to peptide-loaded H-2 K$^b$ or various H-2 K$^{bm}$ mutant molecules, the T2 system was chosen since it is not complicated by the expression of MHC molecules from the parental cell line. Similar to RMA-S $L^d$ cells, T2 cells also express empty MHC molecules that can be readily loaded with different peptides. For these studies peptide-loaded T2 cells transfected with: H-2 T2 K$^b$; H-2 K$^{bm3}$, T2 K$^{b11}$; and H-2 K$^{bm11}$, T2 K$^{bm11}$ were utilized. Tallquist et al., *Journal of Immunology* 155:2419-2426 (1995); Tallquist et al., *Journal of Experimental Medicine* 184:1017-1026 (1996).

Figure 11:
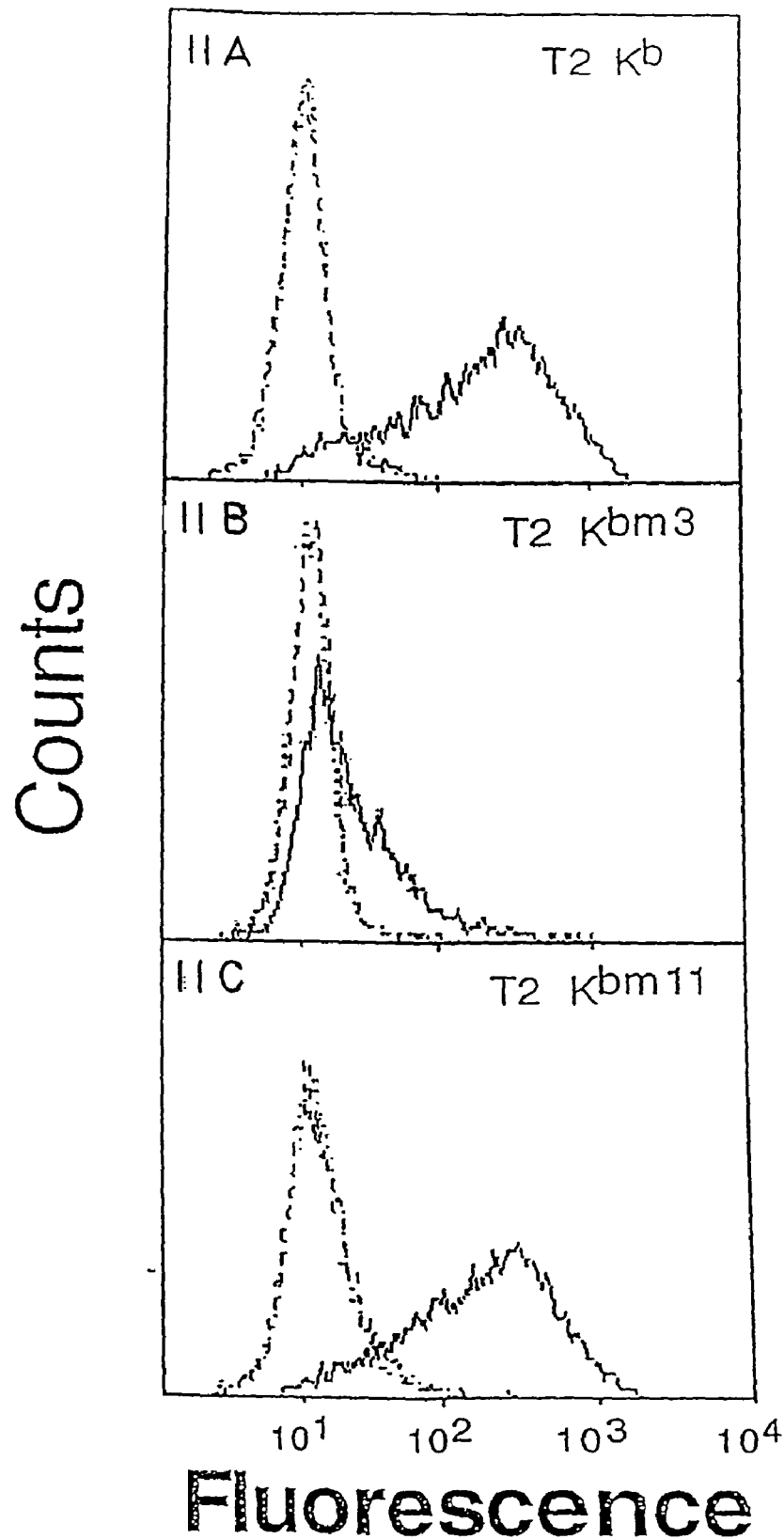
FIG. 11. Fluorescence data showing that soluble divalent 2C TCR/Ig interacts with SIY/MHC complexes but not with dEV-8/MHC complexes. To cells transfected with either H-2 $K^b$, H-2 $K^{bm3}$, or H-2 $K^{bm11}$ were incubated overnight at 27° C. and loaded with peptides dEV-8 (dashed line), SIY (solid line), or pVSV (dotted line), as described below. Cells were stained with purified 2C TCR/Ig (~50 µg/ml) and GAM-IgG-RPE as described in Methods, and analyzed by FACS. Resultant histograms are shown; Panel A, T2-Kb cells; B, T2-K$^{bm3}$; C, T2-K$^{bm11}$. In the histograms presented, 2C TCR/Ig reactivity with either dEV-8 (dashed line) or pVSV (dotted line) was virtually identical, leading to difficulty in discriminating between these two histograms.
Figure 12:
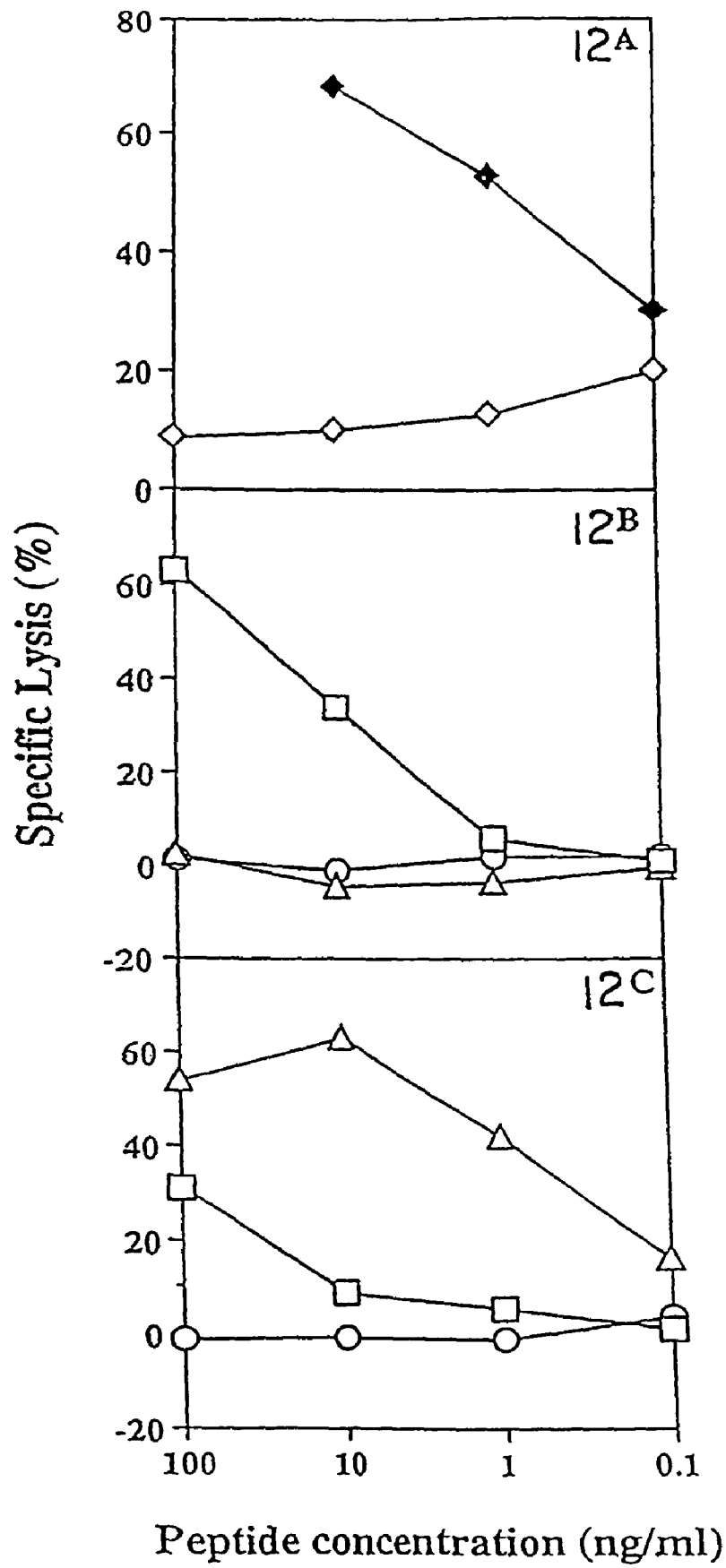
FIG. 12. 2C CTL mediated lysis on various peptide/MHC targets. T2 cells transfected with either H-2 L$^d$ (FIG. 12A), H-2.1K$^b$ (FIG. 12B), or H-2 K$^{bm3}$ (FIG. 12C), were chromium labeled as described and then loaded with peptides by incubating at 25° C. for 1.5 hours in the presence of variable amounts of peptides: p2Ca (♦) and pMCMV (◊) (FIG. 12A); and dEV-8 (Δ); SIY (□); or pVSV (○) (FIGS. 12B and 12C). Peptide-loaded target cells were then incubated at an effector to target ratio of 10:1 and specific lysis calculated as described below. Data shown are representative of three separate experiments.
Figure 13:
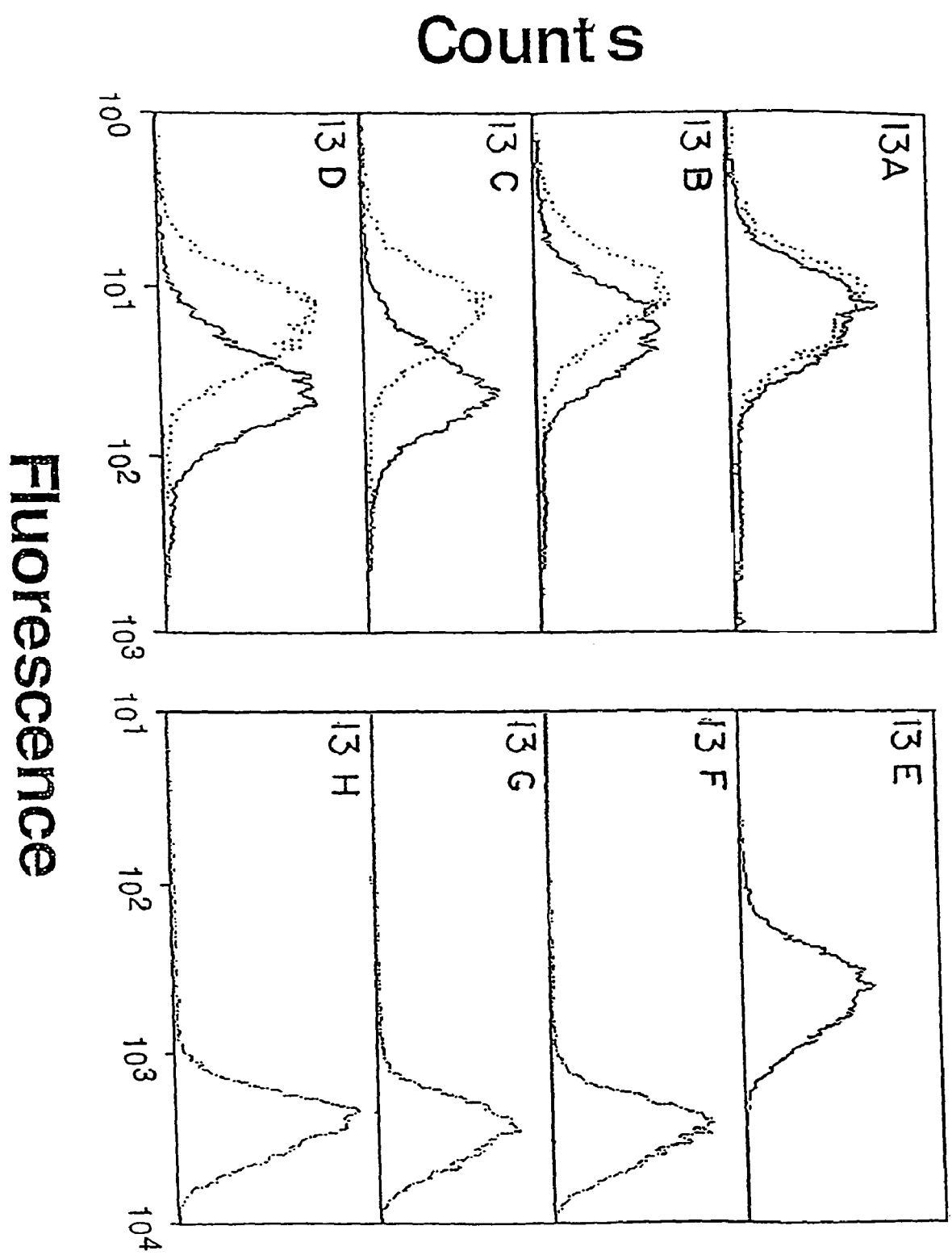
FIG. 13. Fluorescence data showing modulation of endogenous 2C specific peptide/H-2 L$^d$ complexes on the surface of RENCA cells by γ-IFN. RENCA cells were cultured for 48 hours with 0 (FIGS. 13A and 13E), 5 (FIGS. 13B and 13F), 10 (FIGS. 13C and 13G), or 50 (FIGS. 13D and 13H) units/ml γ-IFN. As described, γ-IFN is known to have a direct effect on class I expression, making it necessary to establish background binding of 2C TCR/Ig to γ-IFN treated cells. This was accomplished by incubating RENCA cells with saturating amounts of the H-2 L$^d$ binding peptide, MCMV, which efficiently displaced the endogenous H-2 L$^d$ bound peptides, including any 2C-reactive peptides. Cells were harvested, stained with 2C TCR/Ig (75 mg/ml), FIGS. 13A-D, or the mAb 30.5.7 (45 mg/ml), FIGS. 13E-H, as described below. Cells were subsequently stained with GAM-IgG-RPE and analyzed by FACS. Resultant histograms are shown: Solid lines represent histograms of cultures with no added peptide while dotted lines represent histograms from cultures incubated with pMCMV. All experiments were done in duplicate and repeated at least three times. Note the differences in the extent of fluorescence (see the scales on the histograms) upon staining with 2C-TCR/Ig vs. staining with 30.5.7.

Peptide SIY-loaded T2 K$^b$ or T2 K$^{bm11}$ cells both expressed epitopes recognized by 2C TCR/Ig (FIGS. 11A and 11C). MCF of cells incubated with 2C TCR/Ig increased approximately 20 fold from 14 for pVSV loaded-to 276 for SIY loaded-T2 K$^b$ and from 16 for pVSV loaded- to 250 for SIY-loaded T2 K$^{bm11}$. SIY-loaded T2 K$^{bm3}$ cells showed a much weaker but still significant interaction with 2C TCR/Ig (FIG. 11B); compare SIY-loaded (solid lines; MCF, 36) to pVSV-loaded (dotted lines; MCF, 12) T2 K$^{bm3}$ cells. The 2C TCR/Ig binding data to SIY/MHC complexes was consistent with 2C CTL mediated lysis on various SIY/MHC targets (FIG. 12). 2C CTL mediated efficient lysis of SIY loaded T2 K$^b$ and T2 K$^{bm11}$ cells (FIG. 12B and data not shown, LD50~10 ng/ml for SIY/T2 K$^b$). 2C CTL mediated lysis of SIY loaded T2 K$^{bm3}$ cells was significantly less efficient (FIG. 12C, LD50~100 ng/ml).

The binding of 2C TCR/Ig to dEV-8 loaded cells revealed a striking difference between the affinity of 2C TCR/Ig for dEV-8/MHC complexes and the ability of that same peptide/MHC complex to mediate lysis by 2C CTL. As expected, dEV-8 loaded T2 K$^b$ cells were neither lysed by 2C CTL (FIG. 12B), nor were they recognized by 2C TCR/Ig in flow cytometry assays (FIG. 12A). Interestingly, no significant binding of 2C TCR/Ig could be found to dEV-8 loaded T2 K$^{bm3}$ cells (FIG. 12B). MCF of cells stained with 2C TCR/Ig was similar whether cells were loaded with either dEV-8 or a control H-2 Kb-binding peptide, pVSV (FIG. 12; compare dotted to dashed lines). This is most surprising in that, consistent with previous reports (Tallquist et al., 1996), dEV-8 loaded T2 $K^{bm3}$ cells were efficiently lysed by 2C CTL (FIG. 12C). In fact, dEV-8 loaded T2 $K^{bm3}$ cells were much better target cells (LD50~0.5-1.0 ng/ml), than SIY loaded T2 $K^{bm3}$ cells (LD50 ~100 ng/ml), where a significant binding of 2C TCR/Ig was seen (FIG. 12B). The efficiency of lysis by 2C CTL of dEV-8 loaded T2 $K^{bm3}$ cells, was on the same order of magnitude as that of p2Ca-loaded T2 $L^d$ cells (FIG. 12A, LD50~0.5 ng/ml), which was also efficiently recognized in the 2C TCR/Ig binding assay (FIG. 8). A similar, although significantly less dramatic, lack of correlation between cytolysis and 2C TCR/Ig binding was seen for dEV-8 loaded T2 $K^{bm11}$ cells. dEV-8-loaded T2 $Kb^{m11}$ cells are relatively poor targets for 2C CTL (Tallquist et al., 1996) (data not shown), but were also not reactive with 2C TCR/Ig in flow cytometry assays (FIG. 11C).

Example 7

This example demonstrates analysis of the effects of γ-IFN on expression of endogenous 2C-specific peptide/MHC complexes.

The specificity and affinity of 2C TCR/Ig for peptide/MHC complexes suggested that one might be able to use this reagent to probe the influence of lymphokines on endogenous, cell surface, peptide/MHC complexes. To analyze this possibility and to follow the expression of endogenous 2C-reactive peptide/H-2 $L^d$ complexes within a heterogeneous peptide/MHC environment, the influence of γ-IFN on the H-2 $L^d$-expressing murine cell line RENCA was studied.

RENCA cells were cultured in the presence of variable amounts of γ-IFN to induce up-regulation of naturally loaded peptide/MHC complexes. 2C TCR/Ig binding to RENCA cells increased as a function of γ-IFN induction (FIGS. 13A-D, solid lines). The effect of γ-IFN was dose dependent with a maximal 2-3 fold increase seen on cells treated with 10 units/ml of γ-IFN. Since γ-IFN is known to have a direct effect on class expression (FIGS. 13E-H) (Hengel et al., Journal of Virology 68:289-297 (1994), it is necessary to normalize for any non-specific 2C TCR/Ig binding secondary to increased expression of H-2 $L^d$. This was accomplished by incubating RENCA cells with a control irrelevant H-2 $L^d$-binding peptide, pMCMV.

Since p2Ca is known to have a weak affinity for H-2 $L^d$ (Sykulev et al., *Immunity* 1:15-22 (1994a) exchange with a higher affinity H-2 $L^d$ binding peptide like pMCMV (Sykulev et al., 1994a) should be very efficient. Therefore, background reactivity of 2C TCR/Ig could be determined by the efficient displacement of endogenous p2Ca or p2Ca-like peptides by incubating the cells with saturating amounts of the control pMCMV peptide. In all cases, 2C TCR/Ig binding could be blocked by prior incubation of cells with the control H-2 $L^d$ binding, pMCMV (FIGS. 13A-D, dotted lines). Prior incubation of RENCA cells with a 2C specific peptide, QL9, induced a dramatic increase in 2C TCR/Ig binding. The results of these experiments indicate that 2C TCR/Ig can be used as a sensitive probe to analyze cell surface expression of endogenous 2C-reactive peptide/MHC complexes.

The effect of γ-IFN on 2C TCR/Ig reactivity was distinct from its effects on 30.5.7 reactivity. At all concentrations analyzed, 5-50 units/ml, γ-IFN induced a 5-6 fold increase in serologically reactive 11-2 $L^d$, as recognized by mAb 30.5.7 (FIGS. 13E-H). MCF of unstimulated RENCA cells was 500, while the MCF of γ-IFN stimulated cells was between 2666 and 3038. The maximal effect of γ-IFN was seen at the lowest dose used in the experiment presented, 5 units/ml, and in other experiments was seen even at dose of γ-IFN as low as 1 unit/ml.

Interestingly, the dose response curve of γ-IFN on 2C TCR/Ig reactivity was shifted. γ-IFN at 5 units/ml had a relatively small but significant effect on 2C TCR/Ig reactivity. Maximal effects of γ-IFN on 2C TCR/Ig reactivity required γ-IFN treatment at 10 units/ml, approximately ten-fold more than needed for maximal effects of γ-IFN on 30.5.7 reactivity. These results indicate a differential effect of γ-IFN on MHC heavy chain expression than that of γ-IFN on specific peptide antigen/MHC complex expression.

These results show that this approach is a general one for producing soluble divalent versions of heterodimeric proteins. Soluble divalent analogs of heterodimeric proteins of this invention are characterized as having high avidity or affinity for their target ligands. The same technology for generating soluble divalent heterodimeric proteins can be used to develop other molecular complexes, including both rodent and human class II HLA molecules and α/β and γ/δ T cell receptors.

Example 8

This example demonstrates peptide specificity of 2C TCR/IgG. To examine potential uses of TCR/IgG molecular complexes, we analyzed the specificity and sensitivity of 2C TCR/Ig recognition for peptide/MHC complexes. Initially, we compared the ability of 2C TCR/IgG to detect specific peptide/MHC complexes using either 2C TCR/IgG or the alloreactive $L^d$-specific mAb, 30.5.7.

For these experiments, the 2C-reactive peptides, p2CA and QL9, were loaded into molecules expressed on T2-0 cells. These cells have a defect in the antigen processing pathway and therefore express empty $L^d$ molecules that serve as a source of molecules that can be homogenously loaded peptides of interest.

Figure 14:
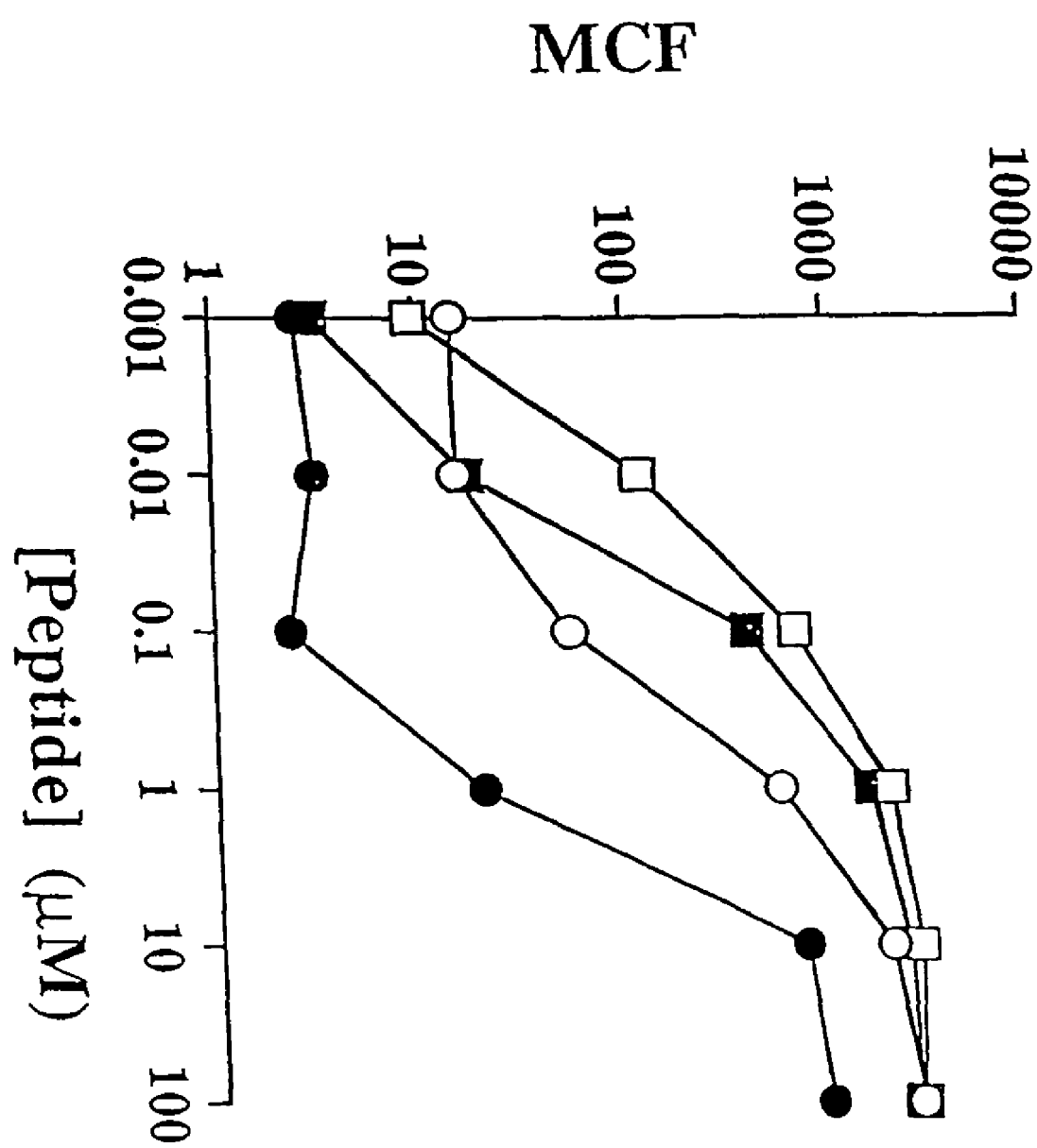
FIG. 14. Comparison of the affinity of 2C TCR/IgG to anti-L$^d$ antibody 30.5.7 and sm2C. RMAS-L$^d$ cells were incubated >15 hours at 27° C. and subsequently incubated for 1.5 hour with the indicated concentration of peptide at 27° C., room temperature. Cells were then incubated for 1.5 hours at 37° C. Peptide-loaded cells were then incubated with 2C TCR/Ig or 30.5.7 (40 µg) for 1 hour, washed, and incubated with GAM/IgG-PE for 1 hr. Cells were then washed and analyzed by flow cytometry. Squares indicate peptide QL9 and circles peptide p2Ca; open symbols represent data from 30.5.7, and closed symbols, 2C TCR/IgG.

2C TCR/IgG binds to peptide-loaded T2-$L^d$ cells in a dose-dependent fashion similar to the binding of mAb 30.5.7 (FIG. 14). Mean channel florescence (MCF) of peptide-loaded cells stained with 2C TCR2IgG increased from a value of 1 to 600 for p2CA loaded cells and to approximately 2500 for QL9-loaded cells, as was observed in previous reports (31, 32), MCF of cells stained with 30.5.7 increased from 500 to approximately 3000 for both p2CA and QL9 loaded T2-$L^d$ cells. 2C TCR/Ig was as sensitive as mAb 30.5.7 in detecting peptide stabilized H2$L^d$ molecules on T2$L^d$ cells. Even the lowest peptide concentration that stabilized sufficient amounts of $L^d$ molecules for recognition by 30.5.7, 0.1 nM QL9 and 1 nM p2CA, also stabilized sufficient amounts of $L^d$ molecules for recognition by 2C TCR/IgG. Thus, 2C TCR/Ig was as sensitive as mAb 30.5.7 at recognizing specific peptide/MHC complexes.

Figure 15:
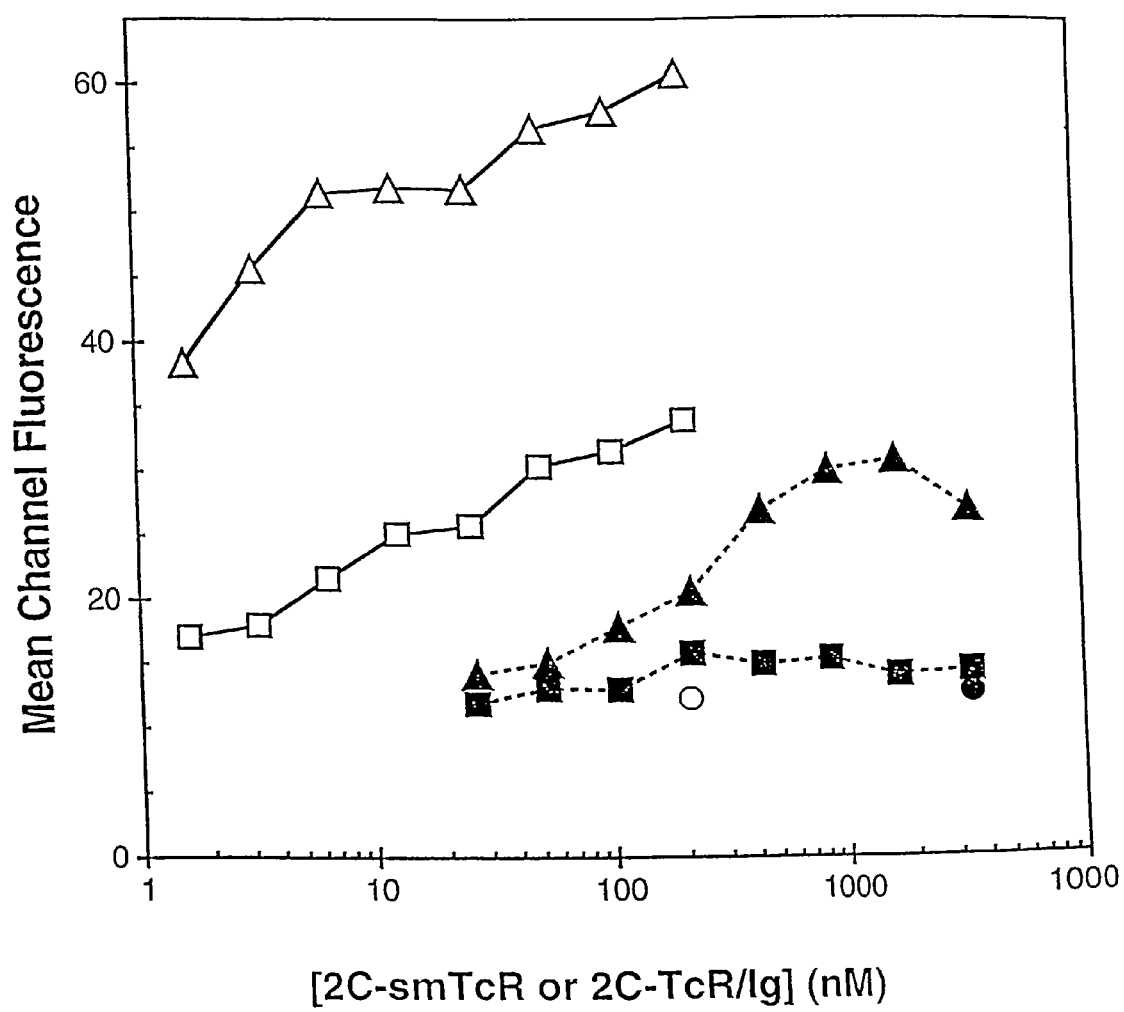
FIG. 15. A comparison of the reactivity of soluble 2C TCR/Ig to that of soluble monovalent 2C TCR with peptide-stabilized H-2 L$^d$ molecules. RMA-S L$^d$ cells were incubated at 27° C. overnight as described. The following morning, peptides, QL9 (Δ), p2Ca (□) or MCMV (○) (final concentration 100 µM) were added to cultures and cell processed as previously described. Cells were stained with serial two-fold dilution of either soluble divalent 2C TCR/Ig superdimer (solid lines) or soluble monovalent 2C TCR (dashed lines). Cells were washed once in FACS wash buffer and then stained with H57-FITC. Cells were incubated for an additional hour and processed as described. To facilitate comparison of cells stained with either 2C TCR/Ig or soluble monovalent 2C TCR, data are presented as mean channel fluorescence. Data shown are from one representative experiment that has been repeated at least three times.

We next compared the ability to use soluble divalent 2C TCR/IgG to soluble monovalent, 2C TCR in flow cytometry. Previously, we had measured the "relative affinities" of these two moieties for cognate peptide/MHC-complexes and had shown that the divalent TCR displays an approximately 50 fold-enhancement in "avidity." Binding of 2C TCR/IgG to QL9-loaded $L^d$ molecules was very sensitive and could be detected even at the lowest concentration tested, 1 nM (FIG. 15). In contrast, greater than 100 nM of soluble monovalent 2C TCR was required to detect binding to QL9-loaded $L^d$ molecules.

The difference in "relative affinity" had an even more dramatic impact on the ability to detect p2CA loaded $L^d$ molecules. Approximately, 3 nM of 2C TCR/IgG was required to detect p2CA-loaded $L^d$ molecules. Even at the highest concentrations tested, 3000 nM, soluble monovalent 2C TCR could not detect p2CA-loaded $L^d$ molecules. $L^d$ molecules loaded with a control peptide, MCMV, were not recognized at any concentration by either soluble monovalent or divalent 2C TCR.

Figure 16:
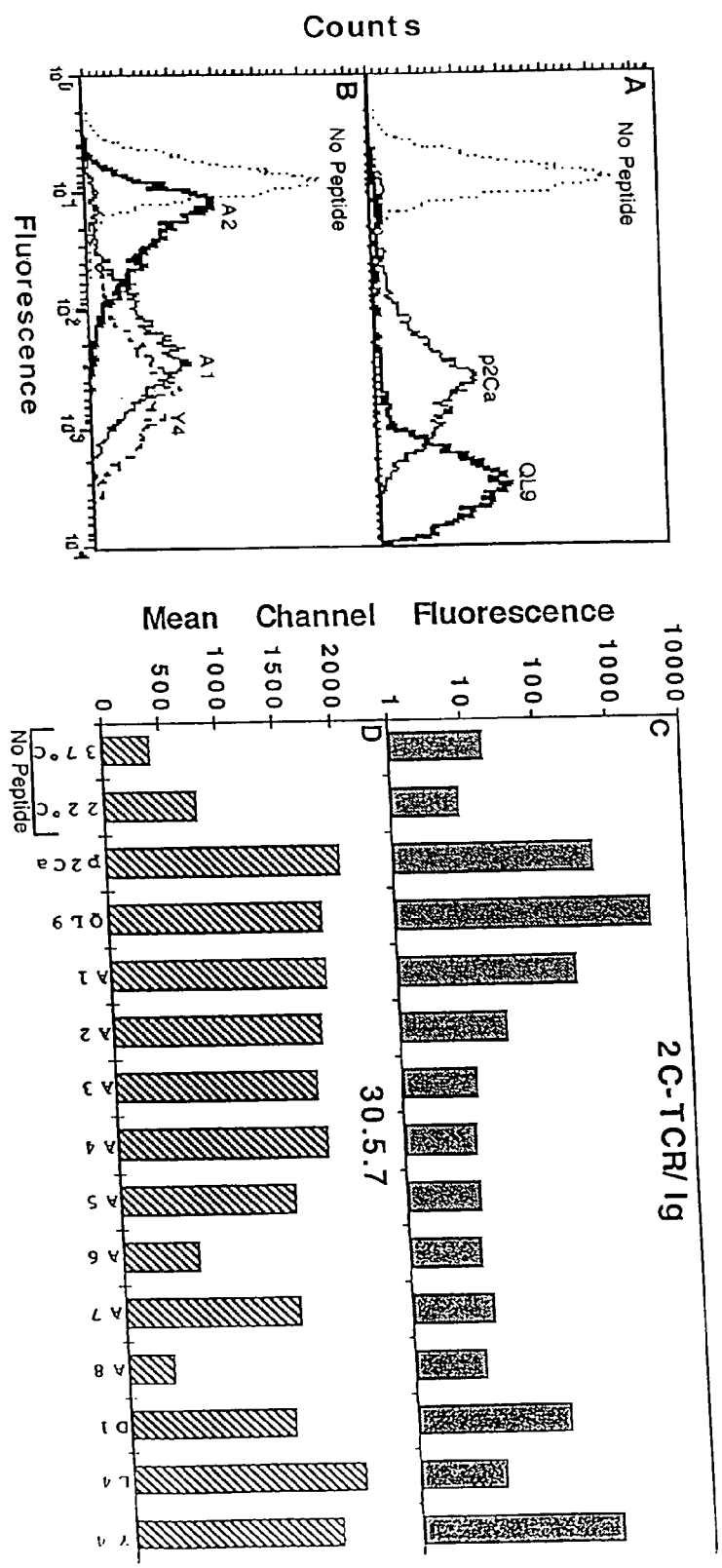
FIG. 16. 2C TCR/IgG has similar sensitivity to 2C CTL as seen in its binding p2Ca variants on RMAS L$^d$ cells. RMAS-L$^d$ cells were incubated with p2Ca or p2Ca-like peptides, as described in FIG. 14. Cells were stained with 2C TCR/Ig and analyzed by flow cytometry. Representative histograms are shown in FIGS. 15A and 15B.

To further demonstrate the efficacy of 2C TCR/Ig in analyzing pepMHC complexes, an array of p2Ca peptide variants bound to $L^d$ were tested in the direct flow cytometry assay (Table 1, FIGS. 16A-16D). As expected, QL9-loaded H-2$L^d$ expressing cells had the highest MCF, ~3000, when stained with 2C TCR/IgG, while p2Ca elicited a signal approximately 10-fold lower (FIGS. 16A and 16C).

Peptide specificity of 2C TCR/IgG was further demonstrated by the differential binding of 2C TCR/Ig to $L^d$ molecules loaded with p2Ca, and its peptide variants, A1-A5, A7, D1, L4 and Y4, (FIGS. 16C and 16D). Specifically, peptide variants A1, A2, D1, L4 and Y4 each stabilized the molecule were all recognized to varying extents by 2C TCR/IgG. $L^d$ molecules loaded with other peptide variants, A3, A4, A5, and A7, could not be detected by 2C TCR/Ig, even though these peptides all stabilized $L^d$ as measured by 30.5.7 binding. These data are similar to the previously published data based on surface plasmon resonance (SPR) (33).

Thus, there were no peptides detected by SPR that were not also recognized by 2C TCR/IgG in the flow cytometry-based assay. Together, these data indicate that 2C TCR/IgG is both a specific and sensitive probe for cognate ligands.

Example 9

This example demonstrates that $^{MCC}$I-$E^k$/IgG binds and activates a cognate T cell hybridoma.

Figure 17:
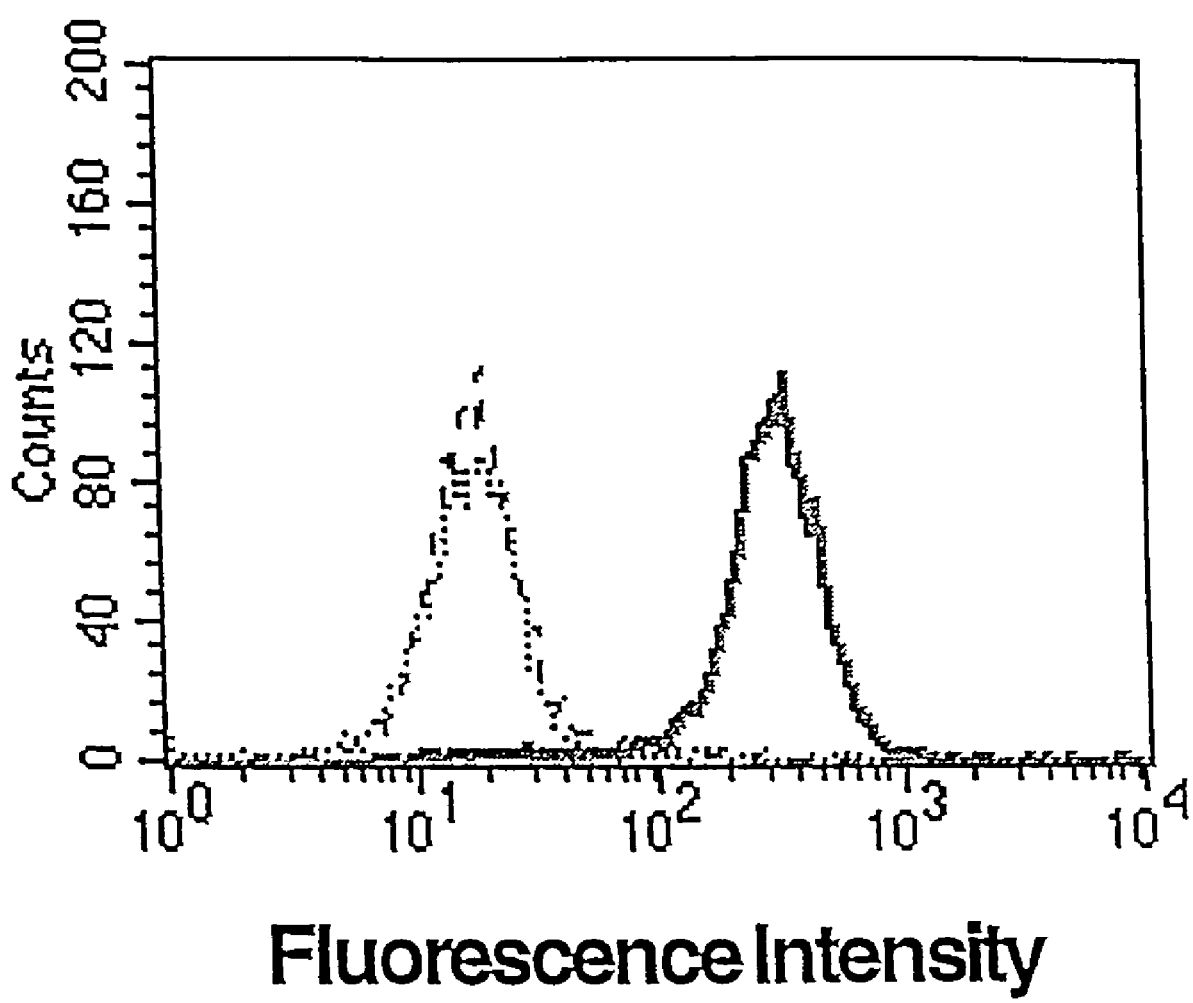
FIG. 17. I-E/IgG binds 5KC cells but not DO11.11 cells. T hybridoma cells, (5KC, Panel A and DO11.10, Panel B) were stained with $^{MCC}$I-E$^k$/Ig (10 µg/sample) for one hour at 4° C. Cells were washed in wash buffer and incubated with GAM/IgG1-PE for another hour at 4 C. Cells were then washed again and analyzed by flow cytometry. Histograms of 5KC cells stained with either $^{MCC}$I-E$^k$/Ig (solid line) or without any primary reagent (dotted line) and of DO11.10 cells stained with $^{MCC}$I-E$^k$/Ig (dashed line) are shown.

To assess the interaction of soluble divalent I-E analogs with antigen specific T cells, we determined whether $^{MCC}$I-$E^k$/IgG could stain antigen specific T cell hybridomas. $^{MCC}$I-$E^k$/IgG binds specifically to 5KC, a moth cytochrome C (MCC)-specific, I-$E^k$-restricted T cell hybridoma (FIG. 17). Mean channel fluorescence of 5KC cells stained with $^{MCC}$I-$E^k$/Ig increased approximate 15-fold, from 19 to 300. Specific staining of 5KC cells was seen with as little as 5 nM of $^{MCC}$I-$E^k$/Ig complexes. In contrast, $^{MCC}$I-$E^k$/Ig complexes did not react with DO11.10, an irrelevant control T cell hybridoma specific for ovalbumin peptide in the context of 1-Ad (FIG. 17), even though both 5KC and DO11.10 expressed the same level of TCR.

Figure 18:
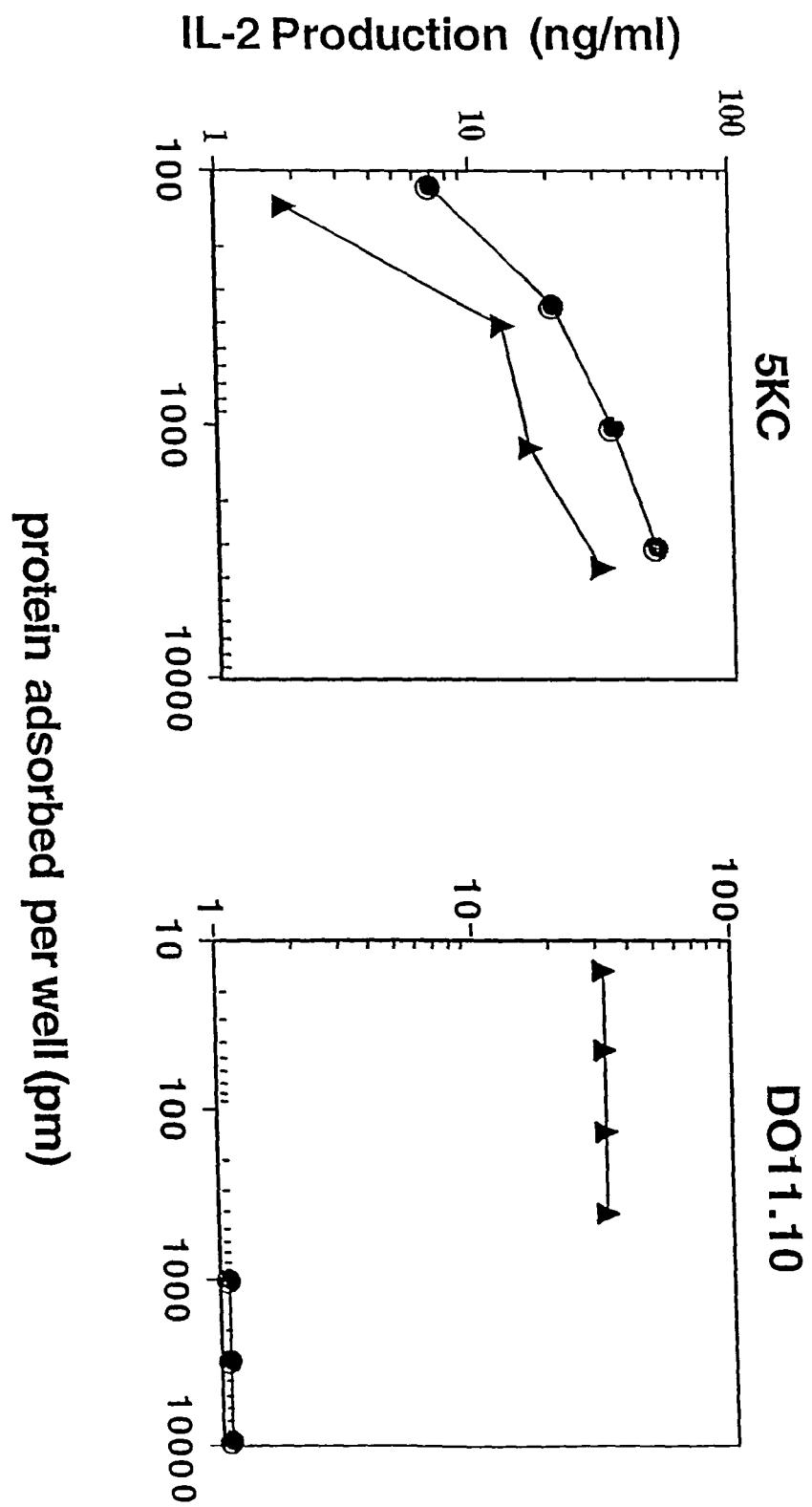
FIG. 18. Immobilized $^{MCC}$I-E$^k$/IgG stimulates IL-2 production by $^{MCC}$I-E$^k$-specific hybridoma, 5KC. Soluble proteins were immobilized on ImmunIon 4 plates at various concentrations and incubated overnight at 4° C. Wells were washed thoroughly, and 5KC T cell hybridoma cells (1×10$^5$) were incubated overnight at 37° C. T cell activation was measured by IL-2 production using an IL-2 ELISA kit.

The biological activity of $^{MCC}$I-$E^k$/IgG was further assessed by comparing the ability of $^{MCC}$I-$E^k$/IgG and anti-CD3 mAb to stimulate the antigen specific T cell hybridomas, 5KC and DO11.10. For these assays, proteins were immobilized on plastic, and activation of 5KC or DO11.10 cells was assayed by lymphokine secretion. Immobilized $^{MCC}$I-$E^k$/IgG stimulated IL-2 production by 5KC but not DO11.10 (FIG. 18). $^{MCC}$I-$E^k$/IgG stimulated 5KC to produce IL-2 at a level comparable to or slightly better than did anti-CD3 mAb. At the lowest concentration tested (92 ng/ml), approximately 10-fold greater stimulation was achieved with $^{MCC}$I-$E^k$/IgG over anti-CD3 mAb.

These results demonstrate that even when immobilized on a plate, soluble divalent $^{MCC}$I-$E^k$/IgG retains its specificity for its cell-surface cognate TCR and is as efficient at activation of antigen-specific T cells as is anti-CD3 mAb.

NUMBERED REFERENCES

1. Garcia, K. C., Degano, M., Pease, L. R, Huang, M., Peterson, P. A., Teyton, L., and Wilson, I. A. (1998) *Science* 279 (February 20), 1166-1172
2. Garboczi, D. N., Ghosh, P., Utz, U., Fan, Q. R., Biddison, W. E., and Wiley, D. C. (1996) *Nature* 384 (November 14), 134-141
3. Garcia, K. C., Degano, M., Stanfield, R. L., Brunmark, A., Jackson, M. R., Peterson, P. A., Teyton, L., and Wilson, I. A. (1996) *Science* 274 (October 11), 209-219
4. Traunecker, A., Dolder, B., Oliveri, Karjalainen, K. (1989) *Immunology Today* 10, 29-32
5. Slanetz, A., and Bothwell, A. L. M. (1991) *Eur. J. Immunol.* 21, 179-183
6. Lin, A. Y., Devaux, B., Green, A., Sagerstrom, C., Elliott, J. F., and Davis, M. M. (1990) *Science* 249, 677-679
7. Wettstein, D. A., Boniface, J. J., Reay, P. A., Schild, H., and Davis, M. M. (1991) *Journal of Experimental Medicine* 174, 219-228
8. Weber, S., Traunecker, A., Oliveri, F., Gerhard, W., and Karjalainen, K. (1992) *Nature* 356, 793-796
9. Soo Hoo, W. F, Lacy, M. J., Denzin, L. K., Voss Jr., E. W., Hardman, K. D., and Kranz, D. M. (1992) *Proc Natl Acad Sci. USA* 89, 4759-4763
10. Plaksin, D., Polakova, K., McPhie, P., and Margulies, D. H. (1997) *J Immunol.* 158, 2218-2227
11. Chang, H.-C., Bao, Z.-Z., Yao, Y., Tse, Coyarts, E. C., Madsen, M., Kawasaki, E., Brauer, P. P., Sacchettini, J. C., Nathenson, S. G., and Reinherz, E. L. (1994) *Proc. Natl. Acad. Sci. USA* 91, 11408-11412
12. Kalandadze, A., Gallen, M., Foncerrada, L., Strominger, J. L., and Wucherpfennig, K. W. (1996) *J. Biol. Chem.* 271(3), 20156-20162
13. Scott, C. A., Garcia, K. C., Carbone, F. R., Wilson, I. A., and Teyton, L. (1996) *Journal of Experimental Medicine* 183 (May), 2087-2095
14. Arimilli, S., Cardoso, C., Mukku, P., Baichwal, V., and Nag, B. (1995) *J. Biol. Chem.* 270(2), 971-977
15. Altman, J. D., Reay, P. A., and Davis, M. M. (1993) *Proc. Natl. Acad. Sci. USA* 90 (November), 10330-10334
16. Dal Porto, J., Johansen, T. E., Catipovic, B., Parfitt, D. J., Tuveson, D., Gether, U., Kozlowski, S., Fearon, D., and Schneck, J. P. (1993) *Proc. Natl. Acad. Sci. USA* 90, 6671-6675
17. O'Herrrin, S. M., Lebowitz, M. S., Bieler, J. G., al-Ramadi, B. K, Utz, U., and Bothwell, A. L. M. (1997) *J. Exp. Med.* 186(8), 1333-1345
18. Altman, J. D., Moss, P. A. R, Goulder, P. J. R., Barouch, McHeyzer-Williams, M. G., Bell, J. L, McMichael, A. J., and Davis, M. M. (1996) *Science* 274 (October 4), 94-96
19. Murali-Krishna, K., Altman, J. D., Suresh, M., Sourdive, D. J. D., Zajac, A. J., Miller, J. D., Slansky, J., and Ahmed, R. (1998) *Immunity* 8 (February), 177-187
20. Haseman, C. A., and Capra, J. D. (1990) *Proc. Natl Acad Sci. USA* 87, 3942-3946
21. Kozono, H., White, J., Clements, J., Maqrrack, P., and Kappler, J. (1994) *Nature* 369, 151-154
22. Finkel, T. R, Marrack, P., Kappler, J. W., Kubo, R. T., and Cambier, J. C. (1989) *J Immunol.* 142, 3006-3012
23. Brodnicki, T. C., Holman, P. O., and Kranz, D. M. (1996) *Molecular Immunology* 33(3), 253-263
24. Kranz, D. M., Sherman, D. H., Sitkovsky, M. V., Pasternack, M. S., and Eisen, H. N. (1984) *Proc. Natl. Acad. Sci. USA* 81 (January), 573-577
25. Catipovic, B., Dal Porto, J., Mage, M., Johansen, T. E., and Schneck, J. P. (1992) *Journal of Experimental Medicine* 176, 1611-1618
26. Hebell, T., Ahearn, J. M., and Fearon, D. T. (1991) *Science* 254, 102-105

27. Lenschow, D. J., Zeng, Y., Thistlehwaite, J. R., Montag, A., Brady, W., Gibson, M. G., Linsley, P. S., and Bluestone, J. A. (1992) *Science* 257, 789-791
28. Finck, B. K., Linsley, P. S., and Wofsy, D. (1994) *Science* 265, 1225-1227
29. Udaka, K., Tsomides, T. J., and Eisen, H. N. (1992) *Cell* 69, 989-998
30. Schwartz, R. H. 91985) *Ann Rev Immunol* 3 237-261
31. Sykulev, Y., Brunmark, A., Jackson, M., Cohen, R. J., Peterson, P. A., and Eisen, H. N. (1994) *Immunity* 1 (April), 15-22
32. Sykulev, T., Brunmark, A., Tsomides, T. J., Kageyama, S., Jackson, M., Peterson, P. A., and Eisen, H. N. (1994) *Proc. Natl. Acad. Sci. USA* 91, 11487-11491
33. Al-Ramadi, B. K., Jelonek, M. T., Boyd, L. F., Margulies, D. H., and Bothwell, A. L. M. (1995) *The Journal of Immunology* 155, 662-673
34. Matsui, K., Boniface, J. J., Beay, P., Schild, H., De St. Groth, B. F., and Davis, M. M. (1991) *Science* 254, 1788-1791
35. Lyons, D. S., Lieberman, S. A., Hampl, J., Boniface, J. J., Chien, Y. -h., Berg, L. J., and Davis, M. M. (1996) *Immunity* 5, 53-61
36. Froscher, B. G., and Klinman, N. R. (1986) *J Exp Med* 164, 196-210
37. Wylie, D. E., Sherman, L. A., and Klinman, N. R. (1982) *Journal of Experimental Medicine* 155 (February), 403-414
38. Leeuwen, Goulmy, E., and Rood, J. J. v. (1979 *Journal of Experimental Medicine* 150, 1075-1083
39. Madden, D. R., Garboczi, D. N., and Wiley, D. C. (1993) *Cell* 75, 693-708
40. Fremont, D. H., Matsumura, M., Sture, E. A., Peterson, P. A., and Wilson, I. A. (1992) *Science* 257, 919-927
41. Bluestone, J. A., Jameson, S., Miller, S., and Dick, R. (1992) *Journal of Experimental Medicine* 176, 1757-1761
42. Andersen, P. S., Stryhn, A., Hansen, B. E., Fugger, L., Engberg, J., and Buus, S. (1996) *Proc. Natl. Acad. Sci. USA* 193 93 (March), 1820-1824
43. Porgador, A., Yewdell, J. W., Deng, Y., Bennink, J. R., and Germain, R. N. (1997) *Immunity* 6 (June), 715-726
44. Dadaglio, G., Nelson, C. A., Deck, M. B., Petzold, S. J., and Unanue, E. R. (1997) *Immunity* 6 (June), 727-738

We claim:

1. A composition comprising a cell in which a molecular complex is bound to the surface of the cell, wherein the molecular complex comprises at least two first fusion proteins and at least two second fusion proteins, wherein:
   (a) each of the two first fusion proteins comprises an immunoglobulin heavy chain, wherein the immunoglobulin heavy chain comprises a variable region, and an extracellular portion of a first transmembrane polypeptide; and
   (b) each of the two second fusion proteins comprises an immunoglobulin light chain and an extracellular portion of a second transmembrane polypeptide;
   wherein the at least two first fusion proteins and the at least two second fusion proteins associate to form the molecular complex, wherein the molecular complex comprises two ligand binding sites, wherein each ligand binding site is formed by the extracellular domain of a first transmembrane polypeptide and the extracellular domain of a second transmembrane polypeptide, wherein the affinity of the molecular complex for a cognate ligand is increased at least two-fold over a dimeric molecular complex consisting of the first and the second fusion protein.

2. The composition of claim 1 wherein the first transmembrane polypeptide is an MHC class IIβ chain and wherein the second transmembrane polypeptide is an MHC class IIα chain.

3. The composition of claim 1 wherein the first transmembrane polypeptide is a TCR α chain and wherein the second transmembrane polypeptide is a TCR β chain.

4. The composition of claim 1 further comprising a pharmaceutically acceptable carrier.

5. The composition of claim 1 wherein a population of the molecular complexes is bound to the cell, wherein an identical antigenic peptide is bound to each ligand binding site.

6. The composition of claim 1 wherein the immunoglobulin heavy chain is an IgG1 heavy chain.

7. The composition of claim 1 wherein the immunoglobulin light chain is an Igκ chain.

8. The composition of claim 1 wherein the first fusion proteins comprise a first peptide linker between the immunoglobulin heavy chain and the extracellular domain of the first transmembrane polypeptide and wherein the second fusion proteins comprise a second peptide linker between the immunoglobulin light chain and the extracellular domain of the second transmembrane polypeptide.

9. The composition of claim 8 wherein the first peptide linker is GLY-GLY-GLY-THR-SER-GLY (SEQ ID NO:10).

10. The composition of claim 8 wherein the second peptide linker is GLY-SER-LEU-GLY-GLY-SER (SEQ ID NO:11).

11. The composition of claim 5 wherein the antigenic peptides are bound to the ligand binding sites by a method comprising the step of:
   incubating the cell in the presence of the antigenic peptides, whereby the antigenic peptides are bound to the ligand binding sites.

12. The composition of claim 5 wherein the antigenic peptides are bound to the ligand binding sites by a method comprising the steps of:
   (a) alkaline stripping of the molecular complex to provide an alkaline stripped molecular complex;
   (b) neutralization of the alkaline stripped molecular complex to provide a neutralized molecular complex;
   (c) incubation of the neutralized molecular complex in the presence of an excess of the antigenic peptides; and
   (d) slow refolding of the neutralized molecular complex in the presence of the excess of the antigenic peptides.

13. The composition of claim 5 wherein the antigenic peptides are covalently bound.

14. A composition comprising a cell in which a molecular complex is bound to the surface of the cell, wherein the molecular complex comprises at least two first fusion proteins and at least two second fusion proteins, wherein:
   (a) each of the two first fusion proteins comprises an immunoglobulin heavy chain, wherein the immunoglobulin heavy chain comprises a variable region, and an extracellular portion of a first transmembrane polypeptide; and
   (b) each of the two second fusion proteins comprises an immunoglobulin light chain and an extracellular portion of a second transmembrane polypeptide;
   wherein the at least two first fusion proteins and the at least two second fusion proteins associate to form the molecular complex, wherein the molecular complex comprises two ligand binding sites, wherein each ligand binding site is formed by the extracellular domain of a first transmembrane polypeptide and the extracellular domain of a second transmembrane polypeptide, wherein the affinity of the molecular complex for a cognate ligand is increased at least two-fold over a dimeric molecular complex consisting of the first and the second fusion protein, wherein the molecular complex is conjugated to a toxin.

15. A composition comprising a cell in which a molecular complex is bound to the surface of the cell, wherein the molecular complex comprises at least two first fusion proteins and at least two second fusion proteins, wherein:

(a) each of the two first fusion proteins comprises an immunoglobulin heavy chain, wherein the immunoglobulin heavy chain comprises a variable region, and an extracellular portion of a first transmembrane polypeptide; and
(b) each of the two second fusion proteins comprises an immunoglobulin light chain and an extracellular portion of a second transmembrane polypeptide;

wherein the at least two first fusion proteins and the at least two second fusion proteins associate to form the molecular complex, wherein the molecular complex comprises two ligand binding sites, wherein each ligand binding site is formed by the extracellular domain of a first transmembrane polypeptide and the extracellular domain of a second transmembrane polypeptide, wherein the affinity of the molecular complex for a cognate ligand is increased at least two-fold over a dimeric molecular complex consisting of the first and the second fusion protein, wherein the molecular complex is conjugated to a lymphokine or other effector molecule which stimulates an immune response.

* * * * *

UNITED STATES PATENT AND TRADEMARK OFFICE
CERTIFICATE OF CORRECTION

| | | |
|---|---|---|
| PATENT NO. | : 7,973,137 B1 | Page 1 of 1 |
| APPLICATION NO. | : 09/642660 | |
| DATED | : July 5, 2011 | |
| INVENTOR(S) | : Schneck et al. | |

It is certified that error appears in the above-identified patent and that said Letters Patent is hereby corrected as shown below:

In the Related U.S. Application Data:

Delete "09/074,276" and insert --09/063,276--

Signed and Sealed this
Ninth Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,973,137 B1 | Page 1 of 1 |
| APPLICATION NO. | : 09/642660 | |
| DATED | : July 5, 2011 | |
| INVENTOR(S) | : Schneck et al. | |

It is certified that error appears in the above-identified patent and that said Letters Patent is hereby corrected as shown below:

Title Page, Item (63) Related U.S. Application Data:

Delete "09/074,276" and insert --09/063,276--

This certificate supersedes the Certificate of Correction issued August 9, 2011.

Signed and Sealed this
Thirtieth Day of August, 2011

David J. Kappos
*Director of the United States Patent and Trademark Office*

```
                        SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO: 1:

CTGTCAGTAA CTGCAGGTGT CCACTCTGGT ACCAGCGGTG AGGTTCAGCT TCAGCAGTCT      60

GGAGC                                                                 65

(2) INFORMATION FOR SEQ ID NO: 2:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO: 2:

AGCCTCTCCC ACTCTCCTGG TAAATGAGCA TGCTCTCAGT GTCCTTGGAG CCCTCTGGTC      60

(2) INFORMATION FOR SEQ ID NO: 3:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (xi) SEQUENCE DESCRIPTION: SEQ ID NO: 3:

CTGTTGCTCT GTTTTCAAGG TACCAGGTGT GGAAGCTTGG GAGGATCTGA TATCCAGATG      60

ACGCAAATCC ATCC                                                       74

(2) INFORMATION FOR SEQ ID NO: 4:
```

(i) SEQUENCE CHARACTERISTICS:
            (A) LENGTH: 66 base pairs
            (B) TYPE: nucleic acid
            (C) STRANDEDNESS: single
            (D) TOPOLOGY: linear (xi) SEQUENCE DESCRIPTION: SEQ ID NO: 4:

GTCAAGAGCT TCAACAGGAA TGAGTGTTAG GGTACCAGAC AAAGGTCCTG AGACGCCACC        60

ACCAGC                                                                  66

(2) INFORMATION FOR SEQ ID NO: 5:

(i) SEQUENCE CHARACTERISTICS:
            (A) LENGTH: 58 base pairs
            (B) TYPE: nucleic acid
            (C) STRANDEDNESS: single
            (D) TOPOLOGY: linear (xi) SEQUENCE DESCRIPTION: SEQ ID NO: 5:

CAGATATGAA CCTAAACTTT CAAGGAGGAG GTACCTGTCA GTTATGGGAC TCCGAATC          58

(2) INFORMATION FOR SEQ ID NO: 6:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (xi) SEQUENCE DESCRIPTION: SEQ ID NO: 6:

CCAAAGAGAC CAGTATCCTG ACTCGAGGAA GCATGTCTAA CACTGCCTTC                   50

(2) INFORMATION FOR SEQ ID NO: 7:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (xi) SEQUENCE DESCRIPTION: SEQ ID NO: 7:

CTGCAACCAT CCTCTATGAG ATCGGAAGCT TAGGATCTGG TACCTACTGG GGAAGGCCAC        60

CCTATATGC                                                               69

(2) INFORMATION FOR SEQ ID NO: 8:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (xi) SEQUENCE DESCRIPTION: SEQ ID NO: 8:

GGTAGCGACC GGCGCTCAGC TGGAATTCAA GCTTCCATTC TCTTTAGTTT CTGGGAGGAG        60

GGT                                                                     63

(2) INFORMATION FOR SEQ ID NO: 9:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (xi) SEQUENCE DESCRIPTION: SEQ ID NO: 9:

```
GCACAGTCCA CATCTGCACA GAACAAGGGA GGAGGTACCG GGGATCCGGT TATTAGTACA      60

TTTATTAAG                                                              69
```

(2) INFORMATION FOR SEQ ID NO: 10:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 10:

```
Gly Gly Gly Thr Ser Gly
1               5
```

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 11:

```
Gly Ser Leu Gly Gly Ser
1               5
```

(2) INFORMATION FOR SEQ ID NO: 12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 12:

```
Leu Ser Pro Phe Pro Phe Asp Leu
1               5
```

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 13:

```
Gln Leu Ser Pro Phe Pro Phe Asp Leu
1               5
```

(2) INFORMATION FOR SEQ ID NO: 14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 14:

```
Leu Ser Pro Phe Pro Phe Asp Leu Leu
1               5
```

(2) INFORMATION FOR SEQ ID NO: 15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 15:

Thr Gln Asn His Arg Ala Leu Asp Leu
1            5

(2) INFORMATION FOR SEQ ID NO: 16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 16:

Tyr Pro His Phe Met Pro Thr Asn Leu
1            5

(2) INFORMATION FOR SEQ ID NO: 17:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 17:

Ser Pro Ser Tyr Val Tyr His Gln Phe
1            5

(2) INFORMATION FOR SEQ ID NO: 18:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 18:

Glu Gln Tyr Lys Phe Tyr Ser Val
1            5

(2) INFORMATION FOR SEQ ID NO: 19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 19:

Ser Ile Tyr Arg Tyr Tyr Gly Leu
1            5

(2) INFORMATION FOR SEQ ID NO: 20:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 20:

Arg Gly Tyr Val Tyr Gln Gly Leu
1                5